US012723060B2

(12) United States Patent
Liu et al.

(10) Patent No.: US 12,723,060 B2
(45) Date of Patent: Sep. 1, 2026

(54) PREPARATION METHOD, INTERMEDIATES, AND USE OF CYCLIC PEPTIDE TOXIN ALPHA-AMANITIN AND/OR AMANINAMIDE

(71) Applicants: INNER MONGOLIA UNIVERSITY, Huhhot (CN); INNER MONGOLIA DUHE INNOVATION R & D TECH CO., LTD, Huhhot (CN)

(72) Inventors: Guodu Liu, Huhhot (CN); Xinlong Yan, Huhhot (CN); Zongwei Li, Huhhot (CN); Yanyan Guo, Huhhot (CN); Tao Zhang, Huhhot (CN)

(73) Assignees: INNER MONGOLIA UNIVERSITY, Huhhot (CN); INNER MONGOLIA DUHE INNOVATION R & D TECH CO., LTD, Huhhot (CN)

( * ) Notice: Subject to any disclaimer, the term of this patent is extended or adjusted under 35 U.S.C. 154(b) by 0 days.

(21) Appl. No.: 18/992,453

(22) PCT Filed: Jun. 4, 2024

(86) PCT No.: PCT/CN2024/097211
§ 371 (c)(1),
(2) Date: Jan. 8, 2025

(87) PCT Pub. No.: WO2024/188375
PCT Pub. Date: Sep. 19, 2024

(65) Prior Publication Data

US 2025/0282826 A1 Sep. 11, 2025

(30) Foreign Application Priority Data

Mar. 7, 2024 (CN) ........................ 202410257131.1

(51) Int. Cl.
*C07K 7/56* (2006.01)
*C07K 5/072* (2006.01)
*C07K 5/093* (2006.01)
*C07K 5/113* (2006.01)
*C07K 7/06* (2006.01)

(52) U.S. Cl.
CPC ............ *C07K 7/56* (2013.01); *C07K 5/06113* (2013.01); *C07K 5/0819* (2013.01); *C07K 5/1021* (2013.01); *C07K 7/06* (2013.01)

(58) Field of Classification Search
None
See application file for complete search history.

(56) References Cited

U.S. PATENT DOCUMENTS

2021/0024605 A1 1/2021 Perrin et al.
2023/0039142 A1 2/2023 Siegert et al.

FOREIGN PATENT DOCUMENTS

| | | | |
|---|---|---|---|
| CN | 104862314 | A | 8/2015 |
| CN | 105377304 | A | 3/2016 |
| CN | 108495840 | A | 9/2018 |
| CN | 114080395 | A | 2/2022 |
| CN | 117843727 | A | 4/2024 |
| EP | 3 792 250 | A1 | 3/2021 |
| JP | 2005-082571 | A | 3/2005 |

OTHER PUBLICATIONS

English translation of CN 117843727 A dowloaded from Google Patents on Jun. 25, 2025 (Year: 2025).*
Yao et al. Iodine-Mediated Tryptathionine Formation Facilitates the Synthesis of Amanitins. J. Am. Chem. Soc. 2021, 143, 14322-14331 (Year: 2021).*
Sharma et al. Liquid-Phase Peptide Synthesis (LPPS): A Third Wave for the Preparation of Peptides. Chem. Rev. 2022, 122, 1351-13546 (Year: 2022).*
Pandey et al. Proline Editing: A General and Practical Approach to the Synthesis of Functionally and Structurally Diverse Peptides. Analysis of Steric versus Stereoelectronic Effects of 4-Substituted Prolines on Conformation within Peptides. J Am Chem Soc. Mar. 20, 2013; 135(11): 4333-4363 (Year: 2013).*
Supporting Information for Yao et al. Iodine-Mediated Tryptathionine Formation Facilitates the Synthesis of Amanitins. J. Am. Chem. Soc. 2021, 143, 14322-14331 (Year: 2021).*
CNIPA, Office Action, Application No. 202410257131.1, Apr. 10, 2024.
Luo: "Research advances in biosynthesis of Amanita cyclic peptide toxins", Mycosystema, vol. 39, No. 9, p. 1651-1660, 2020.

* cited by examiner

*Primary Examiner* — Christina Bradley
(74) *Attorney, Agent, or Firm* — WCF IP

(57) ABSTRACT

A preparation method, intermediates, and use of a cyclic peptide toxin α-Amanitin and/or Amaninamide are provided, belonging to the technical field of organic synthesis. A total synthesis method of the cyclic peptide toxin compounds α-Amanitin and Amaninamide is provided, where raw materials and reagents used are easily purchased through commercial channels, the intermediates are stable, and the preparation method shows mild reaction conditions, simple operation process, desirable operability of separation and purification, and high yield. The preparation method also shows important reference and practical value, can achieve gram-scale preparation of the α-Amanitin and Amaninamide, and has excellent industrial prospects. Therefore, the preparation method is of significant application value in the field of cyclic peptide toxin synthesis.

20 Claims, No Drawings

PREPARATION METHOD, INTERMEDIATES, AND USE OF CYCLIC PEPTIDE TOXIN ALPHA-AMANITIN AND/OR AMANINAMIDE

CROSS REFERENCE TO RELATED APPLICATION

The present application is a national stage application of International Patent Application No. PCT/CN2024/097211, filed on Jun. 4, 2024, which claims priority to Chinese Patent Application No. CN202410257131.1 filed with the China National Intellectual Property Administration (CNIPA) on Mar. 7, 2024 and entitled "PREPARATION METHOD, INTERMEDIATES, AND USE OF CYCLIC PEPTIDE TOXIN ALPHA-AMANITIN AND/OR AMANINAMIDE". The disclosure of the two applications is incorporated herein by reference in its entirety.

TECHNICAL FIELD

The present disclosure relates to the technical field of organic synthesis, and in particular to a preparation method, intermediates, and use of a cyclic peptide toxin α-Amanitin and/or Amaninamide.

BACKGROUND

Amatoxin is a cyclic peptide substance isolated from highly toxic mushrooms and belongs to the class of amanita toxins. Amatoxin has a bicyclic octapeptide structure, and includes nine different polypeptides, namely α-Amanitin, β-Amanitin, γ-Amanitin, ε-Amanitin, amanin, amaninamide, amanullin, amanullinic acid, and proamanullin. Among them, α-Amanitin is the most abundant bicyclic octapeptide in the amatoxin series, and its antibody-drug conjugates (ADCs) can be used for cancer treatment. Therefore, research on the chemical properties and applications of α-Amanitin is highly favored.

α-Amanitin, as a highly efficient inhibitor of eukaryotic RNA polymerase II, can block mRNA transcription and protein synthesis and kill rapidly growing and quiescent cells, thus leading to rapid cell degradation and even apoptosis. Currently, the ADCs of α-Amanitin have cured pancreatic cancer in xenograft mice and are moving towards human trials. Medical researchers need sufficient amounts of α-Amanitin to prepare corresponding ADCs for the cancer treatment. α-Amanitin is mainly isolated and extracted from natural poisonous mushrooms, and can also be synthesized by biological fermentation. Since a natural product has a poor extraction and fermentation yield, the market price of α-Amanitin is extremely expensive (about 12,000 yuan (RMB)/mg), which seriously restricts the research of ADCs for α-Amanitin in cancer treatment. The chemical synthesis of α-Amanitin is an effective method that is expected to achieve large-scale production. Since the 1940s, Heinrich Wieland et al. have begun to characterize the structure and properties of α-Amanitin and derivatives thereof, and chemists have also attempted to chemically synthesize α-Amanitin.

However, there is still a lack of efficient and large-scale methods for synthesizing α-Amanitin and derivatives thereof.

SUMMARY

In view of this, an object of the present disclosure is to provide a preparation method, intermediates, and use of a cyclic peptide toxin α-Amanitin and/or Amaninamide. In the present disclosure, the preparation method is a total synthesis method, which has the advantages of easy availability of raw materials, stable intermediates, mild reaction conditions, simple operation process, excellent operability of separation and purification, and high yield.

To achieve the above object, the present disclosure provides the following technical solutions:

The present disclosure provides a method for preparing a cyclic peptide toxin compound α-Amanitin and/or Amaninamide, α-Amanitin having a structure as shown in Formula 1a, and Amaninamide having a structure as shown in Formula 1b:

Formula 1a

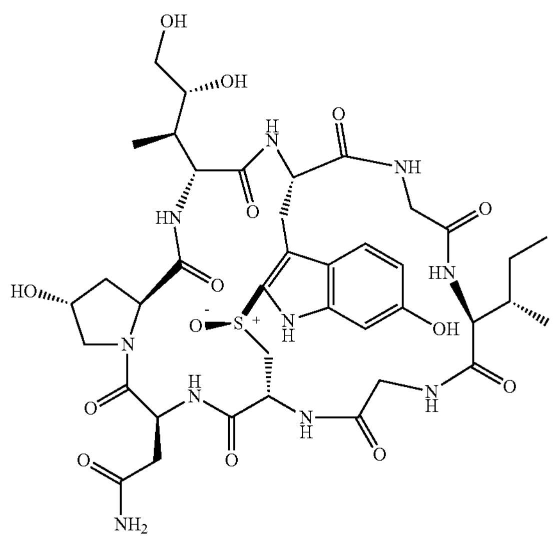

,

Formula 1b

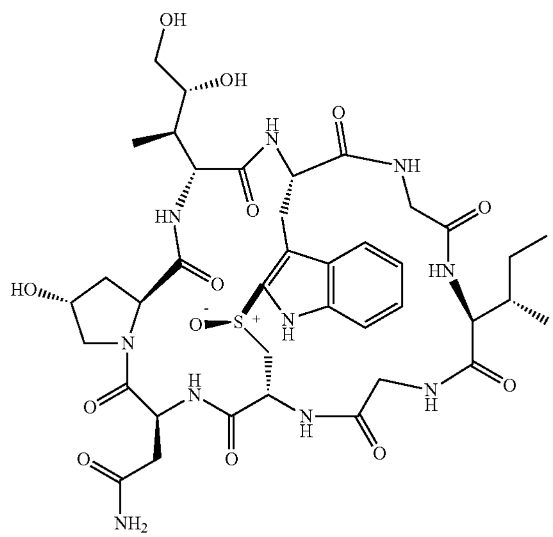

;

where the method includes the following steps:

step 1, subjecting a compound 2 to acetylation and esterification to obtain a compound 3;

step 2, subjecting the compound 3 to condensation and deprotection to obtain a compound 4;

step 3, subjecting the compound 4 to condensation and deprotection to obtain a compound 5;

step 4, subjecting the compound 5 to condensation and deprotection to obtain a compound 6;

step 5, subjecting the compound 6 to condensation and deprotection to obtain a compound 7;

step 6, subjecting the compound 7 to condensation and deprotection to obtain a compound 8;

step 7, subjecting the compound 8 to condensation and deprotection to obtain a compound 9;

step 8, subjecting the compound 9 to condensation and deprotection to obtain a compound 10;

step 9, subjecting the compound 10 to carbon-sulfur bond ring closure in an iodine-mediated manner to obtain a compound 11;

step 10, subjecting the compound 11 to deprotection to obtain a compound 12;

step 11, subjecting the compound 12 to deprotection and condensation to obtain a compound 13;

step 12, subjecting the compound 13 to oxidation to obtain a compound 14; and step 13, subjecting the compound 14 to deprotection to obtain the cyclic peptide toxin compounds α-Amanitin and Amaninamide;

the compounds 2 to 14 have the following structures, respectively:

2

3

4

5

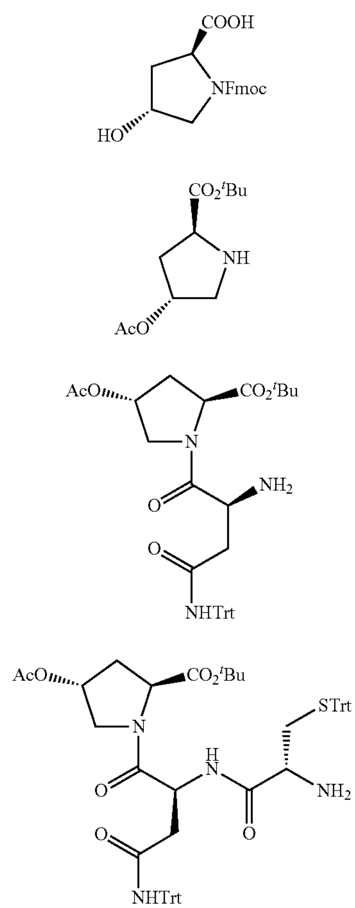

-continued

6

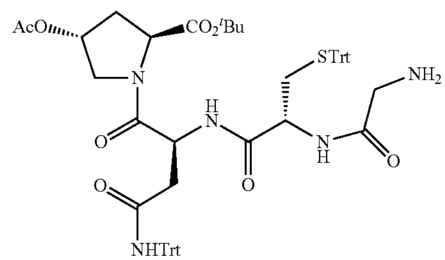

7

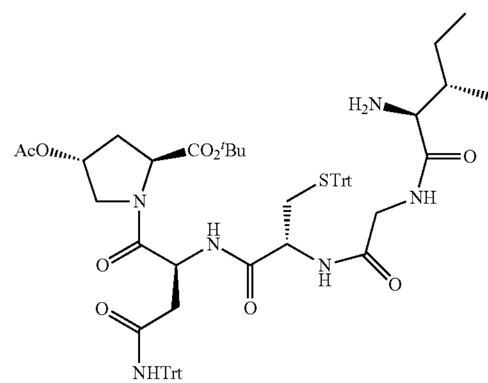

8

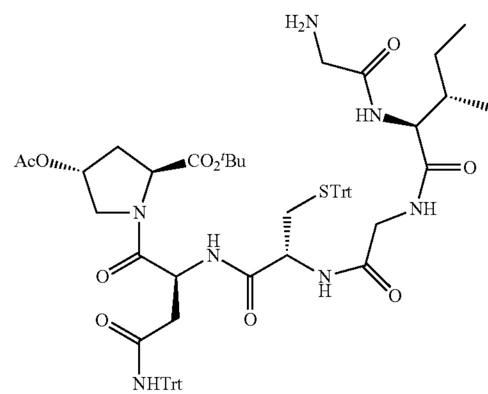

9

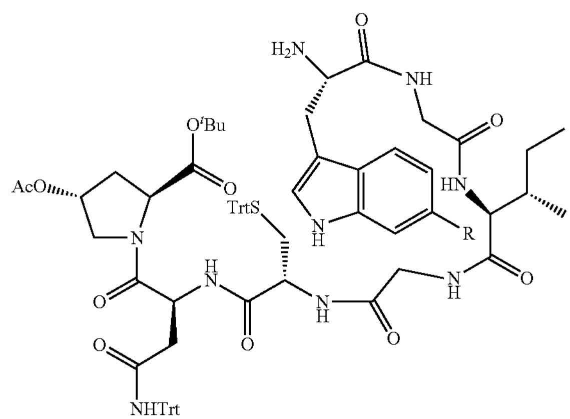

-continued

10

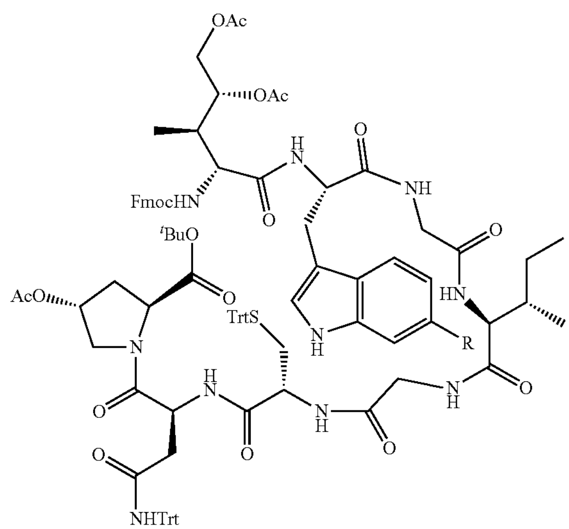

11

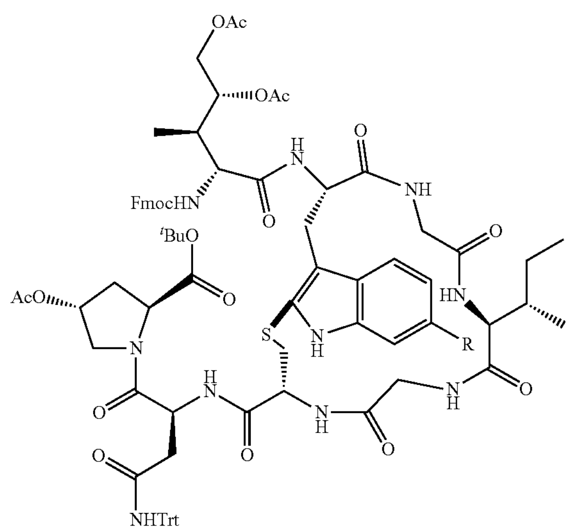

12

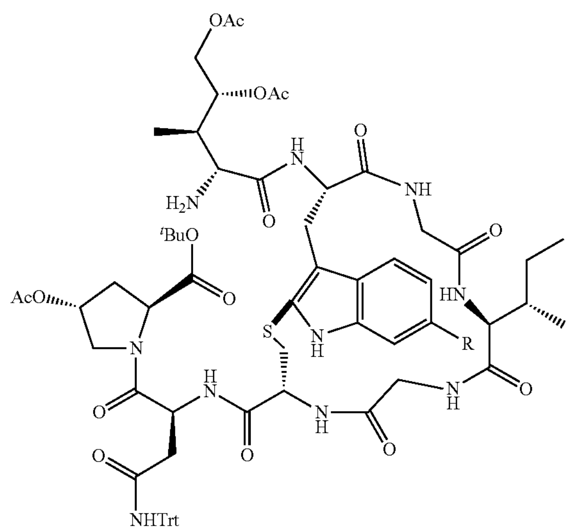

-continued

13

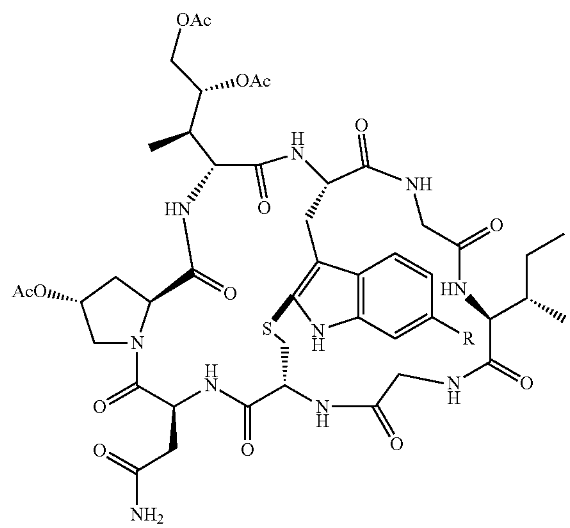

14

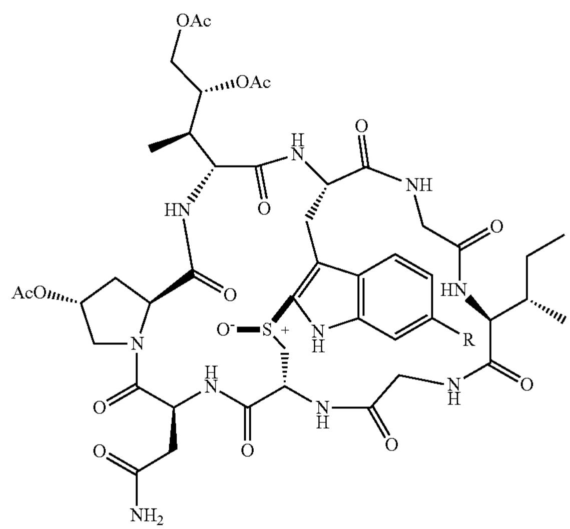

where R in the compounds 9 to 14 is selected from the group consisting of —H and —OBn.

In some embodiments, the method includes the following steps:

step 1, mixing the compound 2, pyridine, acetyl chloride, and an organic solvent, conducting the acetylation to obtain an acetylated product, mixing the acetylated product with N,N-dimethylpyridine and di-tert-butyl dicarbonate (BOC), and conducting the esterification to obtain the compound 3;

step 2, mixing the compound 3, N-fluorenylmethyl (Fmoc)-asparagine, 1-hydroxybenzotriazole, 1-ethyl-(3-dimethylaminopropyl)carbodiimide hydrochloride (EDC-HCl), and an organic solvent, and conducting the condensation and the deprotection to obtain the compound 4;

step 3, mixing the compound 4, N-Fmoc-cysteine, 1-hydroxybenzotriazole, EDC-HCl, and an organic solvent, and conducting the condensation and the deprotection to obtain the compound 5;

step 4, mixing the compound 5, N-Fmoc-glycine, 1-hydroxybenzotriazole, EDC-HCl, and an organic solvent, and conducting the condensation and the deprotection to obtain the compound 6;

step 5, mixing the compound 6, N-Fmoc-isoleucine, 1-hydroxybenzotriazole, EDC-HCl, and an organic solvent, and conducting the condensation and the deprotection to obtain the compound 7;

step 6, mixing the compound 7, N-Fmoc-glycine, 1-hydroxybenzotriazole, EDC-HCl, and an organic solvent, and conducting the condensation and the deprotection to obtain the compound 8;

step 7, mixing the compound 8, a compound 15, 1-hydroxybenzotriazole, EDC-HCl, and an organic solvent, and conducting the condensation and the deprotection to obtain the compound 9, the compound 15 being selected from the group consisting of N-Fmoc-6-benzyloxytryptophan and N-Fmoc-tryptophan;

step 8, mixing the compound 9, a (2S,3R,4R)-4,5-dihydroxyisoleucine derivative, 1-hydroxybenzotriazole, EDC-HCl, and an organic solvent, and conducting the condensation and the deprotection to obtain the compound 10;

step 9, under a protective atmosphere, mixing the compound 10 and an organic solution of iodine, and conducting the carbon-sulfur bond ring closure to obtain the compound 11;

step 10, mixing the compound 11 and an organic solvent, and conducting the deprotection to obtain the compound 12;

step 11, mixing the compound 12, diisopropylethylamine, 2-(7-azabenzotriazol-1-yl)-N,N,N',N'-tetramethyluronium hexafluorophosphate (HATU), and an organic solvent, and conducting the deprotection and the condensation to obtain the compound 13;

step 12, mixing the compound 13, m-chloroperbenzoic acid, and an organic solvent, and conducting the oxidation to obtain the compound 14; and step 13:

under the condition that R is —OBn, subjecting the compound 14, ethanethiol, and a boron trifluoride diethyl etherate solution to a reaction to obtain a crude product, and mixing the crude product and a solution of ammonia in an alcohol, and conducting the deprotection to obtain the α-Amanitin; alternatively, under the condition that R is —H, mixing the compound 14 and the solution of ammonia in the alcohol, and conducting the deprotection to obtain the Amaninamide.

In some embodiments, in step 1, a molar ratio of the compound 2, the acetyl chloride, and the pyridine is in a range of 1:1-3:1-5, and a molar ratio of the compound 2, the N,N-dimethylpyridine, and the BOC is in a range of 1:0.1-1:1-5.

In some embodiments, in step 2, a molar ratio of the compound 3, the N-Fmoc-asparagine, the 1-hydroxybenzotriazole, and the EDC-HCl is 1:1.1:1.1:1.1;

in step 3, a molar ratio of the compound 4, the N-Fmoc-cysteine, the 1-hydroxybenzotriazole, and the EDC-HCl is 1:1.1:1.1:1.1;

in step 4, a molar ratio of the compound 5, the N-Fmoc-glycine, the 1-hydroxybenzotriazole, and the EDC-HCl is 1:1.1:1.1:1.1;

in step 5, a molar ratio of the compound 6, the N-Fmoc-isoleucine, the 1-hydroxybenzotriazole, and the EDC-HCl is 1:1.1:1.1:1.1;

in step 6, a molar ratio of the compound 7, the N-Fmoc-glycine, the 1-hydroxybenzotriazole, and the EDC-HCl is 1:1.1:1.1:1.1;

in step 7, a molar ratio of the compound 8, the compound 15, the 1-hydroxybenzotriazole, and the EDC-HCl is 1:1.1:1.1:1.1; and in step 8, a molar ratio of the compound 9, the (2S,3R,4R)-4,5-dihydroxyisoleucine derivative, the 1-hydroxybenzotriazole, and the EDC-HCl is 1:1.1:1.1:1.1.

In some embodiments, in step 9, a molar ratio of the compound 10 to iodine in the organic solution of iodine is 1:4, and the organic solution of iodine has a concentration of 2 mg/mL.

In some embodiments, in step 10, the organic solvent is a solution of diethylamine (DEA) in dichloromethane (DCM), the DEA in the solution of DEA in DCM has a mass fraction of 50%, and the compound 11 has a concentration of 0.1 g/mL in the solution of DEA in DCM.

In some embodiments, in step 11, a molar ratio of the compound 12, the diisopropylethylamine, and the HATU is 1:2.2:2.

In some embodiments, in step 13, the solution of ammonia in the alcohol has a concentration of 7 mol/L.

In some embodiments, in step 1, the acetylation is conducted at 0° C. for 2 h.

In some embodiments, in step 1, the esterification is conducted at room temperature for 0.5 h.

In some embodiments, in step 2, the condensation and the deprotection are conducted at room temperature for 12 h.

In some embodiments, in step 3, the condensation and the deprotection are conducted at room temperature for 12 h.

In some embodiments, in step 4, the condensation and the deprotection are conducted at room temperature for 12 h.

In some embodiments, in step 5, the condensation and the deprotection are conducted at room temperature for 12 h.

In some embodiments, in step 6, the condensation and the deprotection are conducted at room temperature for 12 h.

In some embodiments, in step 7, the condensation and the deprotection are conducted at room temperature for 12 h.

In some embodiments, in step 8, the condensation and the deprotection are conducted at room temperature for 12 h.

In some embodiments, in step 9, the carbon-sulfur bond ring closure is conducted at room temperature for 1 h.

In some embodiments, in step 10, the deprotection is conducted at room temperature for 1 h.

In some embodiments, in step 11, the condensation and the deprotection are conducted at room temperature for 12 h.

In some embodiments, in step 12, the oxidation is conducted at room temperature for 0.5 h.

In some embodiments, in step 1, after the acetylation is completed, the method further includes: quenching the acetylation with a saturated ammonium chloride solution, adjusting a resulting reaction solution to a pH value of 2 with dilute hydrochloric acid and then extracting three times with DCM to obtain organic phases, combining the organic phases and then drying over anhydrous sodium sulfate, and removing a solvent under reduced pressure to obtain a crude product.

In some embodiments, in step 1, after the esterification is completed, the method further includes: decompressing a resulting product to remove tert-butanol (TBA) to obtain a crude product, dissolving the crude product in a DCM/DEA solution, stirring at room temperature for 1 h, removing a solvent under reduced pressure, and subjecting a resulting material to separation by column chromatography to obtain the compound 3.

In some embodiments, in step 2, after the condensation and the deprotection are completed, the method further includes: washing a resulting organic phase with a saturated sodium carbonate solution, drying over anhydrous sodium sulfate, and removing a solvent under reduced pressure to obtain a crude product; and dissolving the crude product in a DCM/DEA solution, stirred at room temperature for 1 h, removing a solvent under reduced pressure, and subjecting a resulting material to separation by column chromatography to obtain the compound 4.

In some embodiments, in step 3, after the condensation and the deprotection are completed, the method further includes: washing a resulting organic phase with a saturated sodium carbonate solution, drying over anhydrous sodium sulfate, and removing a solvent under reduced pressure to obtain a crude product; and dissolving the crude product in a DCM/DEA solution, stirring at room temperature for 1 h, removing a solvent under reduced pressure, and subjecting a resulting material to separation by column chromatography to obtain the compound 5.

In some embodiments, in step 4, after the condensation and the deprotection are completed, the method further includes: washing a resulting organic phase with a saturated sodium carbonate solution, drying over anhydrous sodium sulfate, and removing a solvent under reduced pressure to obtain a crude product; and dissolving the crude product in a DCM/DEA solution, stirring at room temperature for 1 h, removing a solvent under reduced pressure, and subjecting a resulting material to separation by column chromatography to obtain the compound 6.

In some embodiments, in step 5, after the condensation and the deprotection are completed, the method further includes: washing a resulting organic phase with a saturated sodium carbonate solution, drying over anhydrous sodium sulfate, and removing a solvent under reduced pressure to obtain a crude product; and dissolving the crude product in a DCM/DEA solution, stirring at room temperature for 1 h, removing a solvent under reduced pressure, and subjecting a resulting material to separation by column chromatography to obtain the compound 7.

In some embodiments, in step 6, after the condensation and the deprotection are completed, the method further includes: washing a resulting organic phase with a saturated sodium carbonate solution, drying over anhydrous sodium sulfate, and removing a solvent under reduced pressure to obtain a crude product; and dissolving the crude product in a DCM/DEA solution, stirring at room temperature for 1 h, removing a solvent under reduced pressure, and subjecting a resulting material to separation by column chromatography to obtain the compound 8.

In some embodiments, in step 7, after the condensation and the deprotection are completed, the method further includes: washing a resulting organic phase with a saturated sodium carbonate solution, drying over anhydrous sodium sulfate, and removing a solvent under reduced pressure to obtain a crude product; and dissolving the crude product in a DCM/DEA solution, stirring at room temperature for 1 h, removing a solvent under reduced pressure, and subjecting a resulting material to separation by column chromatography to obtain the compound 9.

In some embodiments, in step 8, after the condensation and the deprotection are completed, the method further includes: washing a resulting organic phase with a saturated sodium carbonate solution, drying over anhydrous sodium sulfate, removing a solvent under reduced pressure to obtain a crude product, and subjecting the crude product to separation by column chromatography to obtain the compound 10.

In some embodiments, in step 9, after the carbon-sulfur bond ring closure is completed, the method further includes: removing N,N-dimethylformamide (DMF) under reduced pressure and recovering to obtain a crude product, and subjecting the crude product to separation by column chromatography to obtain the compound 11.

In some embodiments, in step 10, after the deprotection is completed, the method further includes: removing a solvent under reduced pressure to obtain a crude product, and subjecting the crude product to separation by column chromatography to obtain the compound 12.

The present disclosure further provides intermediates prepared by the method as described above, where the intermediates have the following structures, respectively:

4

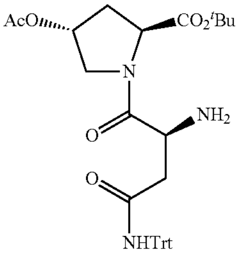

5

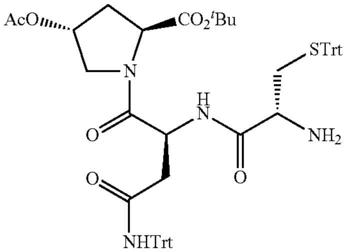

6

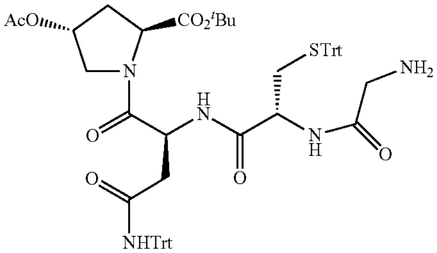

7

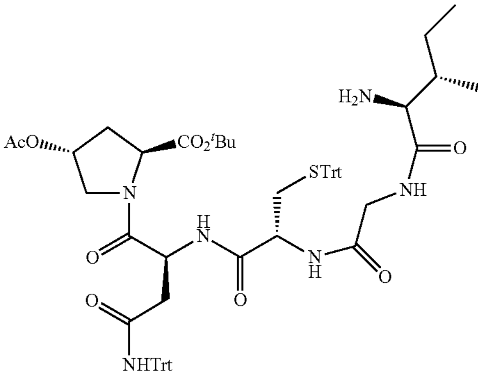

8
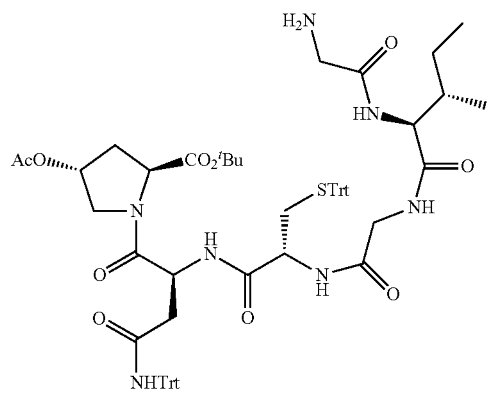
9
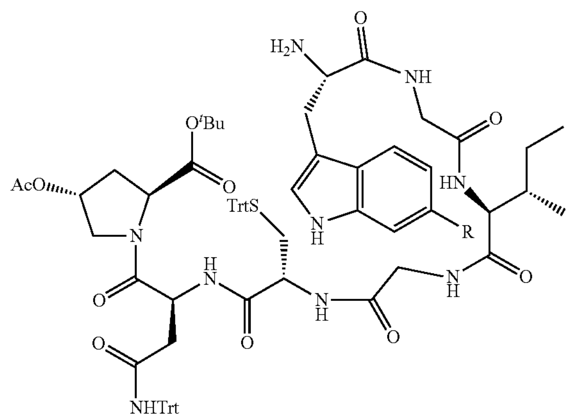
10
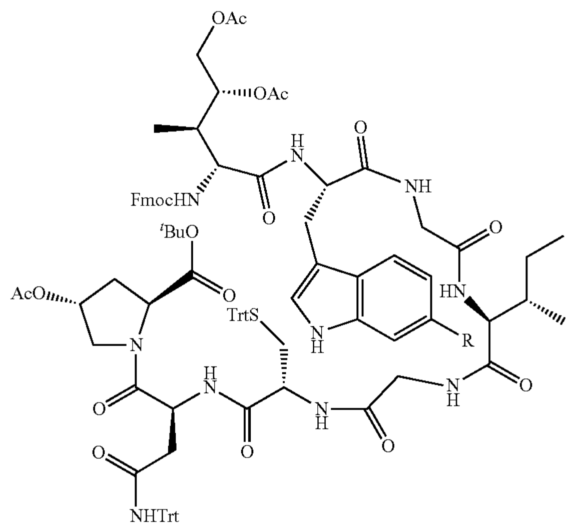
11
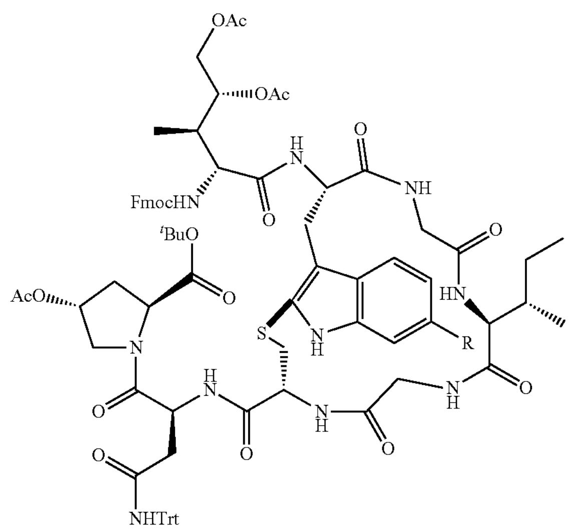
12
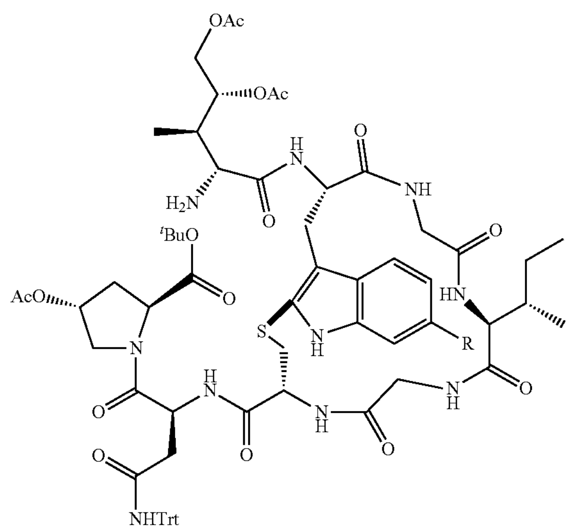
13
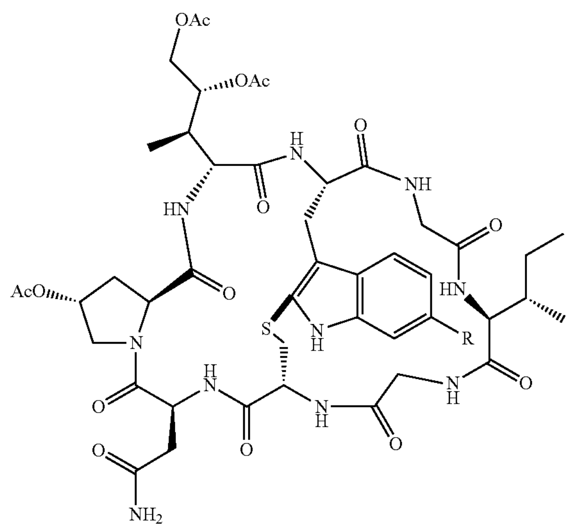

-continued

14

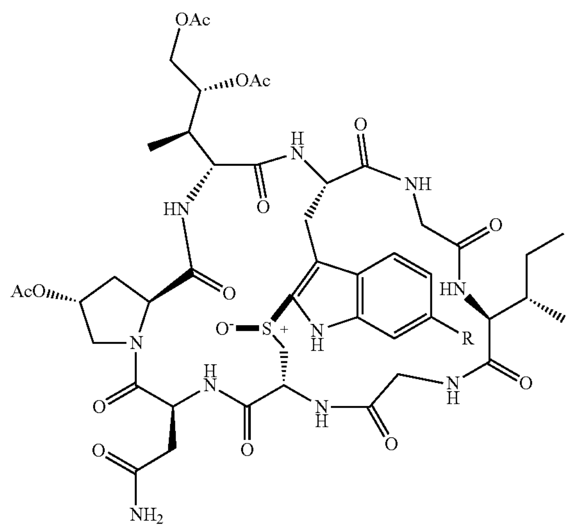

where R in the compounds 9 to 14 is selected from the group consisting of —H and —OBn.

The present disclosure further provides use of the intermediates as described above in preparation of cyclic peptide toxin compounds.

The present disclosure provides a preparation method, intermediates, and use of a cyclic peptide toxin compound α-Amanitin and/or Amaninamide. Compared with the prior art, the present disclosure has the following beneficial effects:

A total synthesis method of the cyclic peptide toxin compounds α-Amanitin and Amaninamide is provided, where raw materials and reagents used are easily purchased through commercial channels, the raw materials have low cost, the intermediates obtained in the synthesis method are stable, and the preparation method shows mild reaction conditions, simple operation process, desirable operability of separation and purification, and high yield. The preparation method also shows important reference and practical value, can achieve gram-scale preparation of the α-Amanitin and Amaninamide. Therefore, the preparation method is of significant application value in the field of cyclic peptide toxin synthesis.

The present disclosure further provides a series of intermediates, which are helpful to promote the synthesis of cyclic peptide toxin compounds and other polypeptide compounds, and have significant application value in the field of polypeptide synthesis.

DETAILED DESCRIPTION OF THE EMBODIMENTS

The present disclosure provides a method for preparing a cyclic peptide toxin compound α-Amanitin and/or Amaninamide, α-Amanitin having a structure as shown in Formula 1a, and Amaninamide having a structure as shown in Formula 1b:

Formula 1a

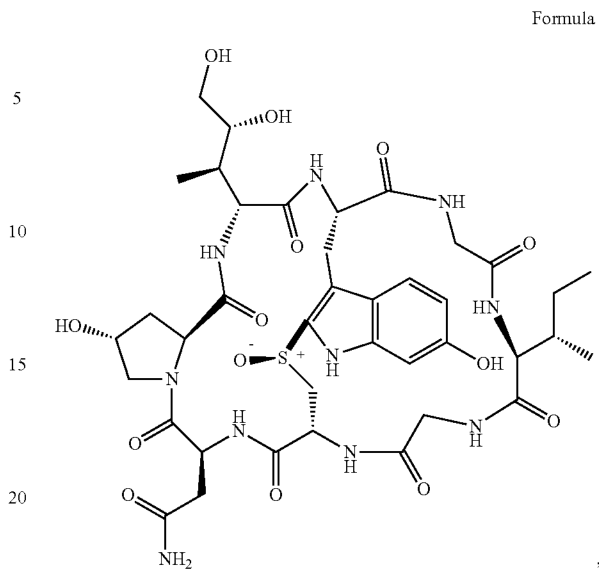

,

Formula 1b

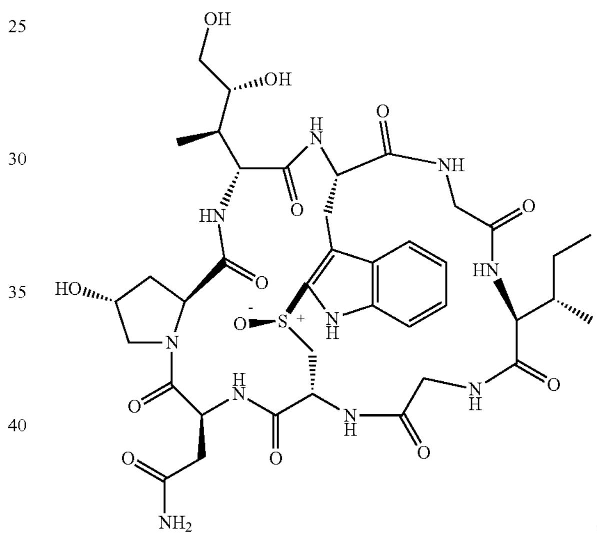

;

where the method includes the following steps:

step 1, subjecting a compound 2 to acetylation and esterification to obtain a compound 3;

step 2, subjecting the compound 3 to condensation and deprotection to obtain a compound 4;

step 3, subjecting the compound 4 to condensation and deprotection to obtain a compound 5;

step 4, subjecting the compound 5 to condensation and deprotection to obtain a compound 6;

step 5, subjecting the compound 6 to condensation and deprotection to obtain a compound 7;

step 6, subjecting the compound 7 to condensation and deprotection to obtain a compound 8;

step 7, subjecting the compound 8 to condensation and deprotection to obtain a compound 9;

step 8, subjecting the compound 9 to condensation and deprotection to obtain a compound 10;

step 9, subjecting the compound 10 to carbon-sulfur bond ring closure in an iodine-mediated manner to obtain a compound 11;

step 10, subjecting the compound 11 to deprotection to obtain a compound 12;

step 11, subjecting the compound 12 to deprotection and condensation to obtain a compound 13;

step 12, subjecting the compound 13 to oxidation to obtain a compound 14; and step 13, subjecting the compound 14 to deprotection to obtain the cyclic peptide toxin compounds α-Amanitin and Amaninamide;

the compounds 2 to 14 each have the structures described above.

In the present disclosure, unless otherwise specified, the raw materials used are all commercially available commodities well known to those skilled in the art or prepared by methods well known to those skilled in the art.

In the present disclosure, the method is carried out according to a principle shown in the following formula:

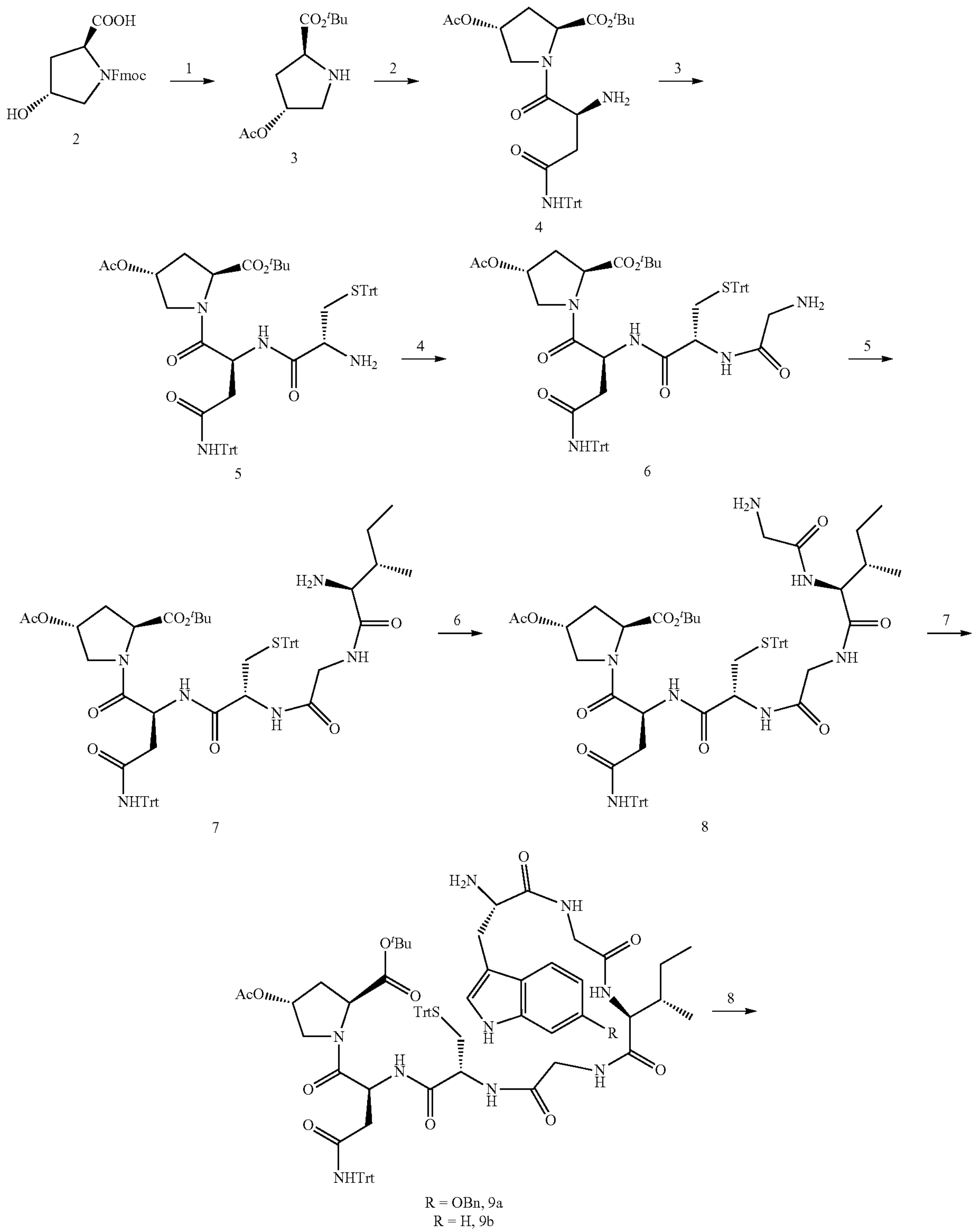

2 3 4 5 6 7 8

R = OBn, 9a
R = H, 9b

-continued
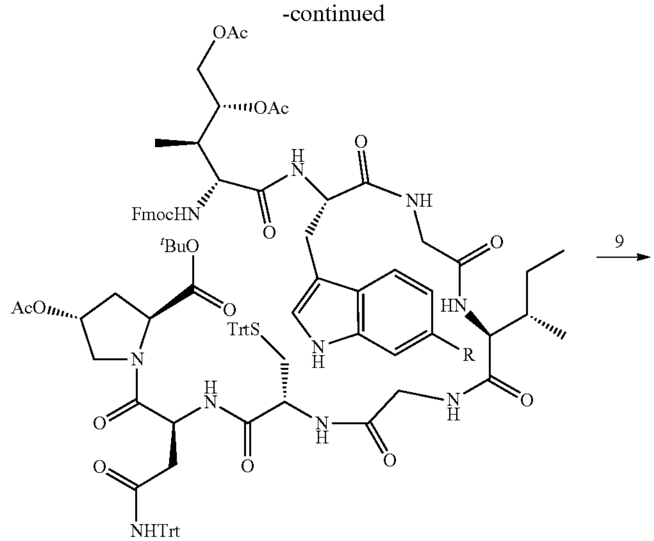
R = OBn, 10a
R = H, 10b
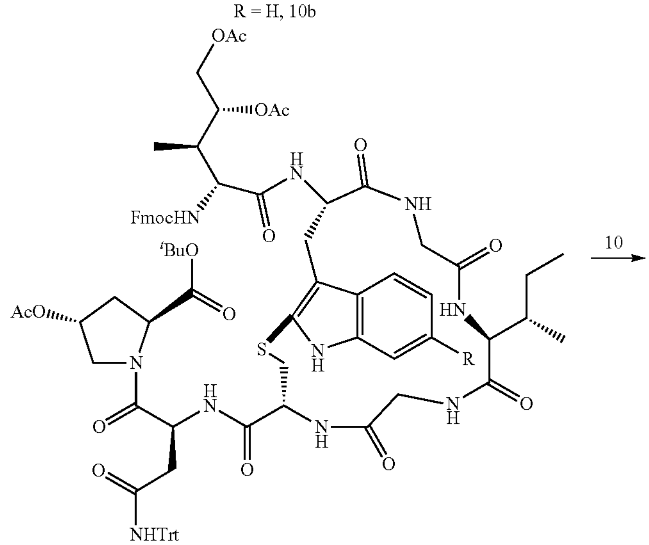
R = OBn, 11a
R = H, 11b
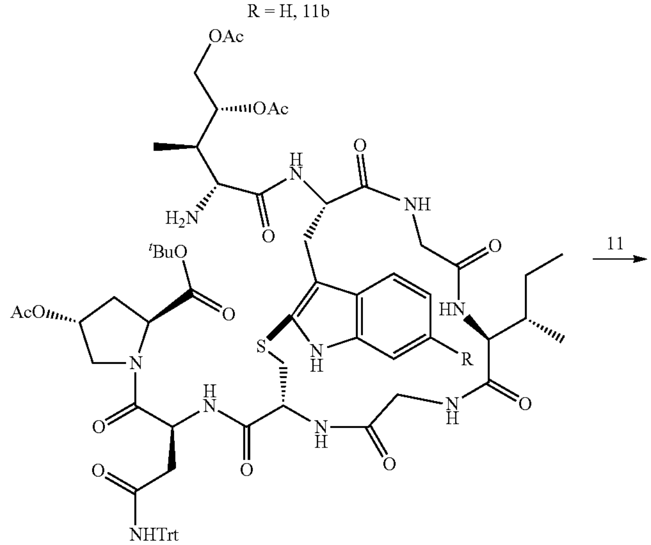
R = OBn, 12a
R = H, 12b -continued

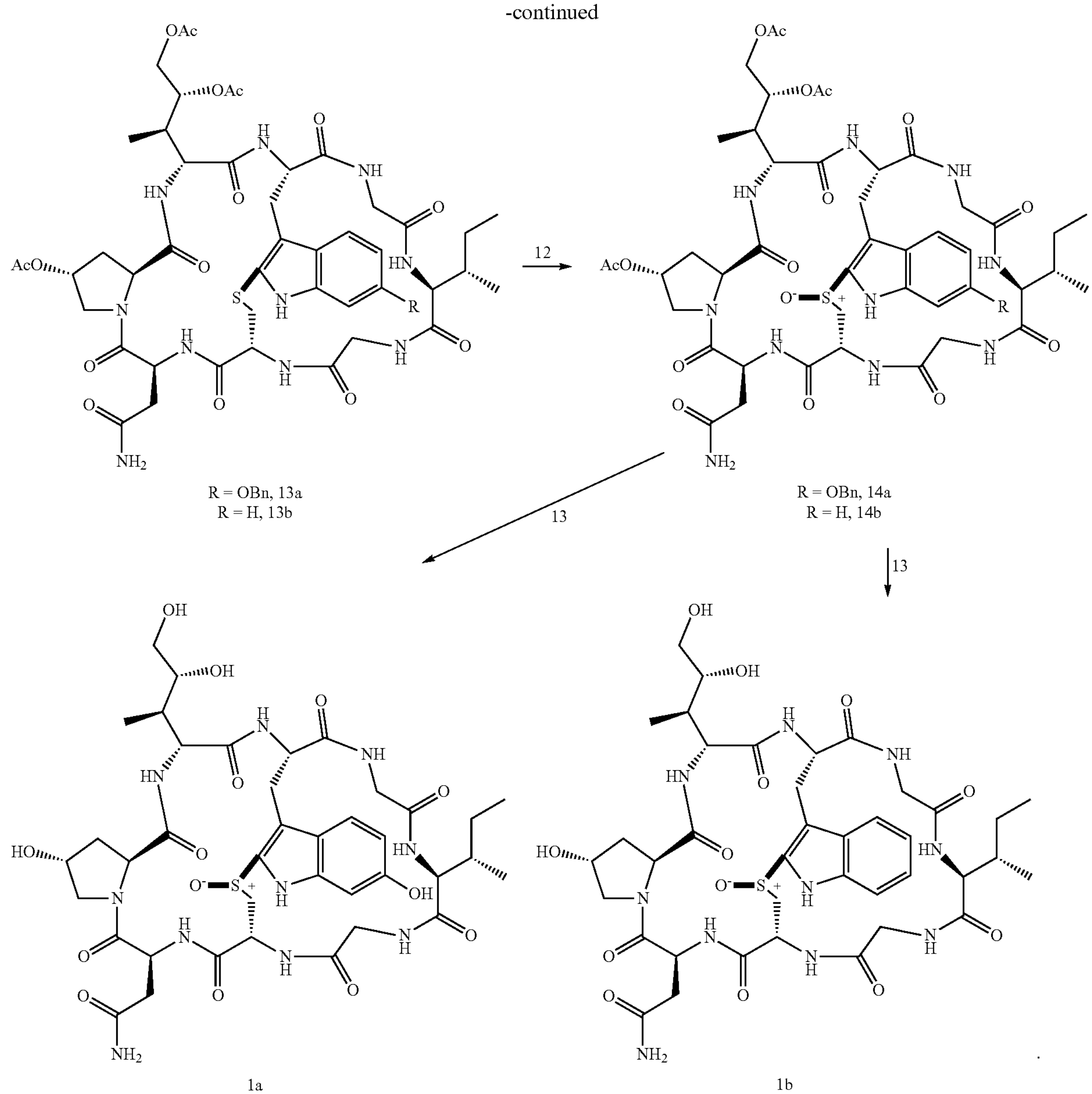

R = OBn, 13a
R = H, 13b

R = OBn, 14a
R = H, 14b

1a

1b

In the present disclosure, in the compounds, Fmoc represents a fluorenylmethoxycarbonyl group, Ac represents an acetyl group, Trt represents a trityl group, and Bn represents a benzyl group.

In some embodiments of the present disclosure, the method includes the following steps:

step 1, mixing the compound 2, pyridine, acetyl chloride, and an organic solvent, conducting the acetylation to obtain an acetylated product, mixing the acetylated product with N,N-dimethylpyridine and di-tert-butyl dicarbonate (BOC), and conducting the esterification to obtain the compound 3;

step 2, mixing the compound 3, N-Fmoc-asparagine, 1-hydroxybenzotriazole, 1-ethyl-(3-dimethylamino-propyl)carbodiimide hydrochloride (EDC-HCl), and an organic solvent, and conducting the condensation and the deprotection to obtain the compound 4;

step 3, mixing the compound 4, N-Fmoc-cysteine, 1-hydroxybenzotriazole, EDC-HCl, and an organic solvent, and conducting the condensation and the deprotection to obtain the compound 5;

step 4, mixing the compound 5, N-Fmoc-glycine, 1-hydroxybenzotriazole, EDC-HCl, and an organic solvent, and conducting the condensation and the deprotection to obtain the compound 6;

step 5, mixing the compound 6, N-Fmoc-isoleucine, 1-hydroxybenzotriazole, EDC-HCl, and an organic solvent, and conducting the condensation and the deprotection to obtain the compound 7;

step 6, mixing the compound 7, N-Fmoc-glycine, 1-hydroxybenzotriazole, EDC-HCl, and an organic solvent, and conducting the condensation and the deprotection to obtain the compound 8;

step 7, mixing the compound 8, a compound 15, 1-hydroxybenzotriazole, EDC-HCl, and an organic solvent, and conducting the condensation and the deprotection to obtain the compound 9, the compound 15 being selected from the group consisting of N-Fmoc-6-benzyloxytryptophan and N-Fmoc-tryptophan;

step 8, mixing the compound 9, a (2S,3R,4R)-4,5-dihydroxyisoleucine derivative, 1-hydroxybenzotriazole, EDC-HCl, and an organic solvent, and conducting the condensation and the deprotection to obtain the compound 10;

step 9, mixing the compound 10 and an organic solution of iodine, and conducting the carbon-sulfur bond ring closure under a protective atmosphere to obtain the compound 11;

step 10, mixing the compound 11 and an organic solvent, and conducting the deprotection to obtain the compound 12;

step 11, mixing the compound 12, diisopropylethylamine, 2-(7-azabenzotriazol-1-yl)-N,N,N',N'-tetramethyluronium hexafluorophosphate (HATU), and an organic solvent, and conducting the deprotection and the condensation to obtain the compound 13;

step 12, mixing the compound 13, m-chloroperbenzoic acid, and an organic solvent, and conducting the oxidation to obtain the compound 14; and step 13:

under the condition that R is —OBn, subjecting the compound 14, ethanethiol, and a boron trifluoride diethyl etherate solution to a reaction to obtain a crude product, and mixing the crude product and a solution of ammonia in an alcohol, and conducting the deprotection to obtain the α-Amanitin; alternatively, under the condition that R is —H, mixing the compound 14 and the solution of ammonia in the alcohol, and conducting the deprotection to obtain the Amaninamide.

In the present disclosure, unless otherwise specified, all the raw materials used are commercially available products conventional in the art.

In the present disclosure, the compound 2, pyridine, acetyl chloride, and an organic solvent are mixed, and subjected to the acetylation to obtain an acetylated product, and the acetylated product is mixed with N,N-dimethylpyridine and BOC, and subjected to the esterification to obtain the compound 3.

In some embodiments of the present disclosure, in step 1, a molar ratio of the compound 2, the acetyl chloride, and the pyridine is in a range of 1:1-3:1-5, and preferably 1:1.5:1.5.

In some embodiments of the present disclosure, the organic solvent is DCM, and preferably dry DCM.

In some embodiments of the present disclosure, the acetylation is conducted at 0° C., and the acetylation is conducted for 2 h.

In some embodiments of the present disclosure, the compound 2 is dissolved in the dry DCM, and the pyridine and the acetyl chloride are added thereto under an ice-bath condition.

In some embodiments of the present disclosure, after the acetylation is completed, the method further includes: quenching the acetylation with a saturated ammonium chloride solution, adjusting a resulting reaction solution to a pH value of 2 with dilute hydrochloric acid and then extracting three times with DCM to obtain organic phases, combining the organic phases and then drying over anhydrous sodium sulfate, and removing a solvent under reduced pressure to obtain a crude product, denoted as the acetylation.

In some embodiments of the present disclosure, a molar ratio of the compound 2, the N,N-dimethylpyridine and the BOC is in a range of 1:0.1-1:1-5, and preferably 1:0.3:2.

In some embodiments of the present disclosure, the esterification is conducted at room temperature, and the esterification is conducted for 0.5 h.

In some embodiments of the present disclosure, the crude product is dissolved in TBA, and the N,N-dimethylpyridine and the BOC are added thereto, and subjected to the esterification.

In some embodiments of the present disclosure, after the esterification is completed, a resulting product is decompressed to remove TBA to obtain a crude product, the crude product is dissolved in a DCM/DEA solution (DCM in the DCM/DEA solution has a mass fraction of 50%), stirred at room temperature for 1 h, a solvent is removed under reduced pressure, and a resulting material is subjected to separation by column chromatography to obtain the compound 3.

In the present disclosure, after the compound 3 is obtained, the compound 3, N-Fmoc-asparagine, 1-hydroxybenzotriazole, EDC-HCl, and an organic solvent are mixed, and subjected the condensation and the deprotection to obtain the compound 4.

In some embodiments of the present disclosure, a molar ratio of the compound 3, the N-Fmoc-asparagine, the 1-hydroxybenzotriazole, and the EDC-HCl is 1:1.1:1.1:1.1.

In some embodiments of the present disclosure, the organic solvent is dry DCM.

In some embodiments of the present disclosure, the condensation and the reaction deprotection each are conducted at room temperature, and the condensation and the reaction deprotection each are conducted for 12 h.

In some embodiments of the present disclosure, the compound 3 is dissolved in the dry DCM, and the N-Fmoc-asparagine, the 1-hydroxybenzotriazole, and the EDC-HCl are added thereto under an ice-bath condition and then reacted at room temperature for 12 h, a resulting organic phase is washed with a saturated sodium carbonate solution, dried over anhydrous sodium sulfate, and a solvent is removed under reduced pressure to obtain a crude product; and the crude product is dissolved in a DCM/DEA solution (DCM in the DCM/DEA solution has a mass fraction of 50%), stirred at room temperature for 1 h, a solvent is removed under reduced pressure, and a resulting material is subjected to separation by column chromatography to obtain the compound 4.

In the present disclosure, after the compound 4 is obtained, the compound 4, N-Fmoc-cysteine, 1-hydroxybenzotriazole, EDC-HCl, and an organic solvent are mixed, and subjected the condensation and the deprotection to obtain the compound 5.

In some embodiments of the present disclosure, a molar ratio of the compound 4, the N-Fmoc-cysteine, the 1-hydroxybenzotriazole, and the EDC-HCl is 1:1.1:1.1:1.1.

In some embodiments of the present disclosure, the organic solvent is dry DCM.

In some embodiments of the present disclosure, the condensation and the deprotection each are conducted at room temperature, and the condensation and the deprotection each are conducted for 12 h.

In some embodiments of the present disclosure, the compound 4 is dissolved in the dry DCM, and the N-Fmoc-cysteine, the 1-hydroxybenzotriazole, and the EDC-HCl are added thereto under an ice-bath condition and then reacted at room temperature for 12 h, a resulting organic phase is washed with a saturated sodium carbonate solution, dried over anhydrous sodium sulfate, and a solvent is removed under reduced pressure to obtain a crude product; and the crude product is dissolved in a DCM/DEA solution (DCM in the DCM/DEA solution has a mass fraction of 50%), stirred at room temperature for 1 h, a solvent is removed under reduced pressure, and a resulting material is subjected to separation by column chromatography to obtain the compound 5.

In the present disclosure, after the compound 5 is obtained, the compound 5, N-Fmoc-glycine, 1-hydroxybenzotriazole, EDC-HCl, and an organic solvent are mixed, and subjected the condensation and the deprotection to obtain the compound 6.

In some embodiments of the present disclosure, a molar ratio of the compound 5, the N-Fmoc-glycine, the 1-hydroxybenzotriazole, and the EDC-HCl is 1:1.1:1.1:1.1.

In some embodiments of the present disclosure, the organic solvent is dry DCM.

In some embodiments of the present disclosure, the condensation and the deprotection each are conducted at room temperature, and the condensation and the deprotection each are conducted for 12 h.

In some embodiments of the present disclosure, the compound 5 is dissolved in the dry DCM, and the N-Fmoc-glycine, the 1-hydroxybenzotriazole, and the EDC-HCl are added thereto under an ice-bath condition and then reacted at room temperature for 12 h, a resulting organic phase is washed with a saturated sodium carbonate solution, dried over anhydrous sodium sulfate, and a solvent is removed under reduced pressure to obtain a crude product; and the crude product is dissolved in a DCM/DEA solution (DCM in the DCM/DEA solution has a mass fraction of 50%), stirred at room temperature for 1 h, a solvent is removed under reduced pressure, and a resulting material is subjected to separation by column chromatography to obtain the compound 6.

In the present disclosure, after the compound 6 is obtained, the compound 6, N-Fmoc-isoleucine, 1-hydroxybenzotriazole, EDC-HCl, and an organic solvent are mixed, and subjected the condensation and the deprotection to obtain the compound 7.

In some embodiments of the present disclosure, a molar ratio of the compound 6, the N-Fmoc-isoleucine, the 1-hydroxybenzotriazole, and the EDC-HCl is 1:1.1:1.1:1.1.

In some embodiments of the present disclosure, the organic solvent is dry DCM.

In some embodiments of the present disclosure, the condensation and the deprotection each are conducted at room temperature, and the condensation and the deprotection each are conducted for 12 h.

In some embodiments of the present disclosure, the compound 6 is dissolved in the dry DCM, and the N-Fmoc-isoleucine, the 1-hydroxybenzotriazole, and the EDC-HCl are added thereto under an ice-bath condition and then reacted at room temperature for 12 h, a resulting organic phase is washed with a saturated sodium carbonate solution, dried over anhydrous sodium sulfate, and a solvent is removed under reduced pressure to obtain a crude product; and the crude product is dissolved in a DCM/DEA solution (DCM in the DCM/DEA solution has a mass fraction of 50%), stirred at room temperature for 1 h, a solvent is removed under reduced pressure, and a resulting material is subjected to separation by column chromatography to obtain the compound 7.

In the present disclosure, after the compound 7 is obtained, the compound 7, N-Fmoc-glycine, 1-hydroxybenzotriazole, EDC-HCl, and an organic solvent are mixed, and subjected the condensation and the deprotection to obtain the compound 8.

In some embodiments of the present disclosure, a molar ratio of the compound 7, the N-Fmoc-glycine, the 1-hydroxybenzotriazole, and the EDC-HCl is 1:1.1:1.1:1.1.

In some embodiments of the present disclosure, the organic solvent is dry DCM.

In some embodiments of the present disclosure, the condensation and the deprotection each are conducted at room temperature, and the condensation and the deprotection each are conducted for 12 h.

In the present disclosure, the compound 7 is dissolved in the dry DCM, and the N-Fmoc-glycine, the 1-hydroxybenzotriazole, and the EDC-HCl are added thereto under an ice-bath condition and then reacted at room temperature for 12 h, a resulting organic phase is washed with a saturated sodium carbonate solution, dried over anhydrous sodium sulfate, and a solvent is removed under reduced pressure to obtain a crude product; and the crude product is dissolved in a DCM/DEA solution (DCM in the DCM/DEA solution has a mass fraction of 50%), stirred at room temperature for 1 h, a solvent is removed under reduced pressure, and a resulting material is subjected to separation by column chromatography to obtain the compound 8.

In the present disclosure, after the compound 8 is obtained, the compound 8, a compound 15, 1-hydroxybenzotriazole, EDC-HCl, and an organic solvent are mixed, and subjected the condensation and the deprotection to obtain the compound 9, the compound 15 being selected from the group consisting of N-Fmoc-6-benzyloxytryptophan and N-Fmoc-tryptophan.

In some embodiments of the present disclosure, a molar ratio of the compound 8, the compound 15, the 1-hydroxybenzotriazole, and the EDC-HCl is 1:1.1:1.1:1.1.

In some embodiments of the present disclosure, the organic solvent is dry DCM.

In some embodiments of the present disclosure, the condensation and the deprotection each are conducted at room temperature the condensation and the deprotection each are conducted for 12 h.

In the present disclosure, the compound 15 has a structure as shown below:

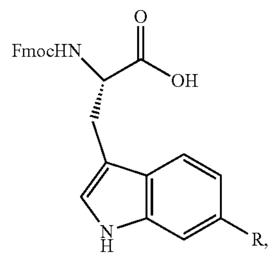

where

R is selected from the group consisting of —OBn and —H;

under the condition that R is —OBn, the compound 15 is the N-Fmoc-6-benzyloxytryptophan; and under the condition that R is —H, the compound 15 is the N-Fmoc-tryptophan.

In some embodiments of the present disclosure, the compound 8 is dissolved in the dry. DCM, and the N-Fmoc-6-benzyloxytryptophan, the 1-hydroxybenzotriazole, and the EDC-HCl are added thereto under an ice-bath condition and then reacted at room temperature for 12 h, a resulting organic phase is washed with a saturated sodium carbonate solution, dried over anhydrous sodium sulfate, and a solvent is removed under reduced pressure to obtain a crude product; and the crude product is dissolved in a DCM/DEA solution (DCM in the DCM/DEA solution has a mass fraction of 50%), stirred at room temperature for 1 h, a solvent is removed under reduced pressure, and a resulting material is subjected to separation by column chromatography to obtain a compound 9a.

In some embodiments of the present disclosure, the compound 8 is dissolved in the dry DCM, and the N-Fmoc-tryptophan, the 1-hydroxybenzotriazole, and the EDC-HCl are added thereto under an ice-bath condition and then reacted at room temperature for 12 h, a resulting organic phase is washed with a saturated sodium carbonate solution, dried over anhydrous sodium sulfate, and a solvent is removed under reduced pressure to obtain a crude product; and the crude product is dissolved in a DCM/DEA solution (DCM in the DCM/DEA solution has a mass fraction of 50%), stirred at room temperature for 1 h, a solvent is removed under reduced pressure, and a resulting material is subjected to separation by column chromatography to obtain a compound 9b.

In the present disclosure, after the compound 9 is obtained, the compound 9, a (2S,3R,4R)-4,5-dihydroxyisoleucine derivative, 1-hydroxybenzotriazole, EDC-HCl, and an organic solvent are mixed, and subjected to the condensation and the deprotection to obtain the compound 10.

In some embodiments of the present disclosure, a molar ratio of the compound 9, the (2S,3R,4R)-4,5-dihydroxyisoleucine derivative, the 1-hydroxybenzotriazole, and the EDC-HCl is 1:1.1:1.1:1.1.

In some embodiments of the present disclosure, the organic solvent is dry DCM.

In some embodiments of the present disclosure, the condensation and the deprotection each are conducted at room temperature, and the condensation and the deprotection each are conducted for 12 h.

In the present disclosure, the (2S,3R,4R)-4,5-dihydroxyisoleucine derivative has a structure shown in Formula 16 (compound 16):

Formula 16

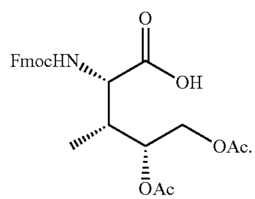

In some embodiments of the present disclosure, the compound 9 is dissolved in the dry DCM, and the (2S,3R,4R)-4,5-dihydroxyisoleucine derivative, the 1-hydroxybenzotriazole, and the EDC-HCl are added thereto under an ice-bath condition and then reacted at room temperature for 12 h, a resulting organic phase is washed with a saturated sodium carbonate solution, dried over anhydrous sodium sulfate, and a solvent is removed under reduced pressure to obtain a crude product; and the crude product is subjected to separation by column chromatography to obtain the compound 10.

In the present disclosure, after the compound 10 is obtained, the compound 10 and an organic solution of iodine are mixed and then subjected to the carbon-sulfur bond ring closure under a protective atmosphere to obtain the compound 11.

In some embodiments of the present disclosure, the protective atmosphere is provided by nitrogen.

In some embodiments of the present disclosure, a molar ratio of the compound 10 and iodine in the organic solution of iodine is 1:4, and the organic solution of iodine has a concentration of 2 mg/mL.

In some embodiments of the present disclosure, a solvent of the organic solution of iodine is DMF.

In some embodiments of the present disclosure, the carbon-sulfur bond ring closure is conducted at room temperature, and the carbon-sulfur bond ring closure is conducted for 1 h.

In the present disclosure, the compound 10 is added into the DMF solution of iodine under a nitrogen atmosphere and subjected to a reaction at room temperature for 1 h, the DMF is removed under reduced pressure and recovered to obtain a crude product, and the crude product is subjected to separation by column chromatography to obtain the compound 11.

In the present disclosure, after the compound 11 is obtained, the compound 11 and an organic solvent are mixed, and subjected to the deprotection to obtain the compound 12.

In some embodiments of the present disclosure, the organic solvent is a solution of DEA in DCM, the DEA in the solution of DEA in DCM has a mass fraction of 50%, and the compound 11 has a concentration of 0.1 g/mL in the solution of DEA in DCM.

In some embodiments the present disclosure, the deprotection is conducted at room temperature, and the deprotection is conducted for 1 h.

In the present disclosure, the compound 11 is dissolved in the DCM/DEA solution, stirred at room temperature for 1 h, a solvent is removed under reduced pressure, and a crude product is subjected to separation by column chromatography to obtain the compound 12.

In the present disclosure, after the compound 12 is obtained, the compound 12, diisopropylethylamine, HATU, and an organic solvent are mixed, and subjected to the deprotection and the condensation to obtain the compound 13.

In some embodiments of the present disclosure, the organic solvent is DMF.

In some embodiments of the present disclosure, a molar ratio of the compound 12, the diisopropylethylamine, and the HATU is 1:2.2:2.

In some embodiments of the present disclosure, the deprotection and the reaction condensation each are conducted at room temperature, and the deprotection and the reaction condensation each are conducted for 12 h.

In some embodiments of the present disclosure, the compound 12 is dissolved in trifluoroacetic acid (TFA), the compound 12 in a resulting system has a concentration of 0.1 g/mL, stirred at room temperature for 1 h, and the TFA is removed under reduced pressure to obtain a crude product; the crude product is dissolved in dry DMF, the diisopropylethylamine and the HATU are added thereto, reacted at room temperature for 12 h, and the DMF is removed under reduced pressure and recovered to obtain a crude product; and the crude product is subjected to separation by column chromatography to obtain the compound 13.

In the present disclosure, after the compound 13 is obtained, the compound 13, m-chloroperbenzoic acid, and an organic solvent are mixed, and subjected to the oxidation to obtain the compound 14.

In some embodiments of the present disclosure, a molar ratio of the compound 13 to the m-chloroperbenzoic acid is 1:1.

In some embodiments of the present disclosure, the organic solvent is a mixed solution of isopropanol and ethanol, and a volume ratio of the isopropanol to the ethanol in the mixed solution of the isopropanol and the ethanol is 2:1.

In some embodiments of the present disclosure, the oxidation is conducted at room temperature, and the oxidation is conducted for 0.5 h.

In some embodiments of the present disclosure, the compound 13 is dissolved in the mixed solution of isopropanol and ethanol, and the compound 13 in a resulting system has a concentration of 0.2 g/mL, the m-chloroperbenzoic acid is added thereto, reacted at room temperature for 0.5 h, a solvent is removed under reduced pressure to obtain a crude product, and the crude product is subjected to separation by column chromatography to obtain the compound 14.

In the present disclosure, after the compound 14 is obtained, under the condition that R is —OBn (namely a compound 14a), the compound 14; ethanethiol, and a boron trifluoride diethyl etherate solution are subjected to a reaction to obtain a crude product, and the crude product and a solution of ammonia in the alcohol are mixed, and subjected to the deprotection to obtain the α-Amanitin.

In some embodiments of the present disclosure, the compound 14a is dissolved in the ethanethiol, the boron trifluoride diethyl etherate solution is added thereto, reacted at room temperature for 1 h, and the ethanethiol is removed under reduced pressure to obtain a crude product; and the crude product is dissolved in a methanol solution of ammonia, reacted at room temperature for 2 h, a solvent is removed under reduced pressure, and an obtained crude product is subjected to separation by column chromatography to obtain a compound 1a.

In some embodiments of the present disclosure, a molar ratio of the compound 14a to boron trifluoride in the boron trifluoride diethyl etherate solution is 1:20; the compound 14a has a concentration of 8 mg/mL in the ethanethiol; the crude product has a concentration of 0.01 g/mL in the methanol solution of ammonia.

In the present disclosure, under the condition that R is —H (namely a compound 14b), the compound 14 and the solution of ammonia in the alcohol are mixed, and subjected to the deprotection to obtain the Amaninamide.

In some embodiments of the present disclosure, the compound 14b is dissolved in the solution of ammonia in the alcohol, reacted at room temperature for 2 h, a solvent is removed under reduced pressure to obtain a crude product, and the crude product is subjected to separation by column chromatography to obtain a compound 1b.

In some embodiments of the present disclosure, the compound 14b has a concentration of 0.01 g/mL in the solution of ammonia in the alcohol.

In some embodiments of the present disclosure, the solution of ammonia in the alcohol has a concentration of 7 mol/L; and the solution of ammonia in the alcohol is a solution of ammonia in methanol.

The present disclosure further provides a series of intermediates, where the intermediates have the following structures, respectively:

4

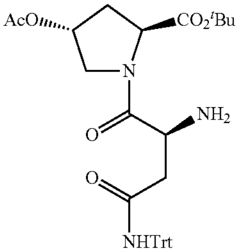

5

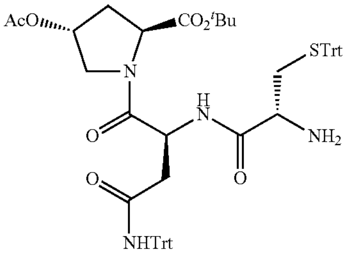

6

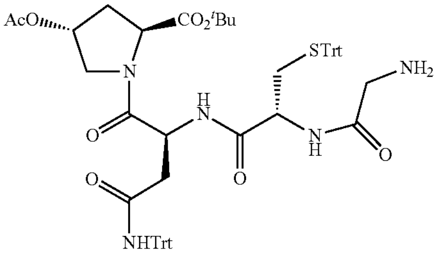

7

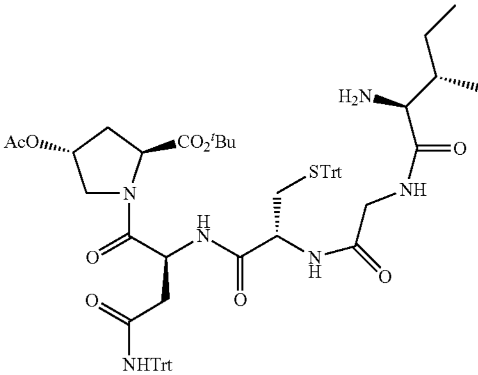

8

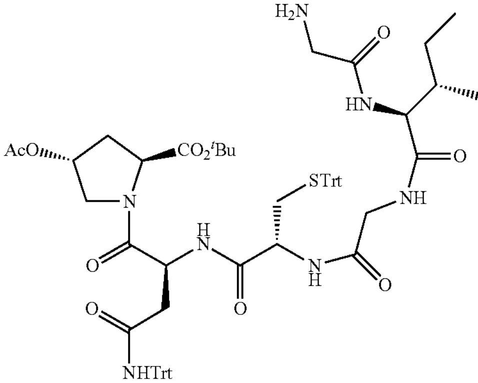

-continued
9
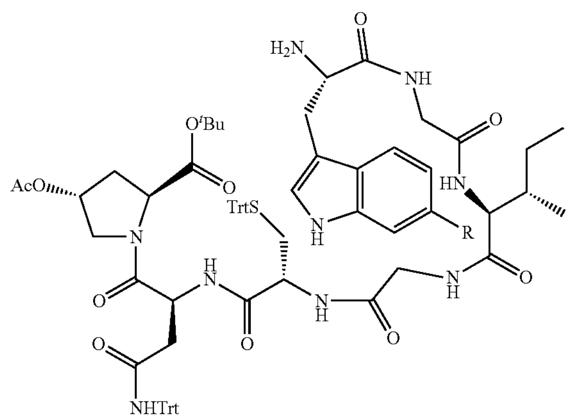
10
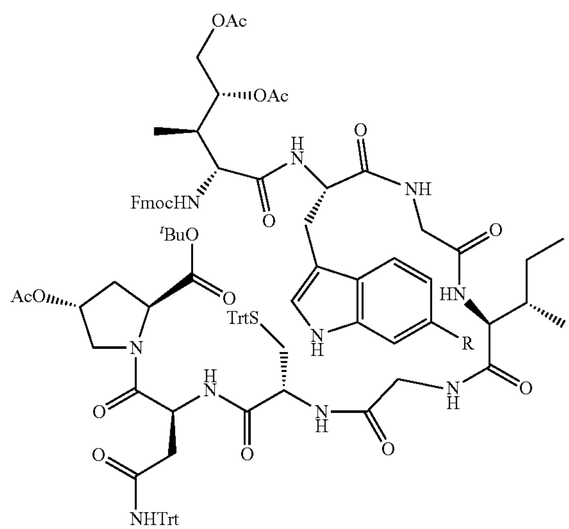
11
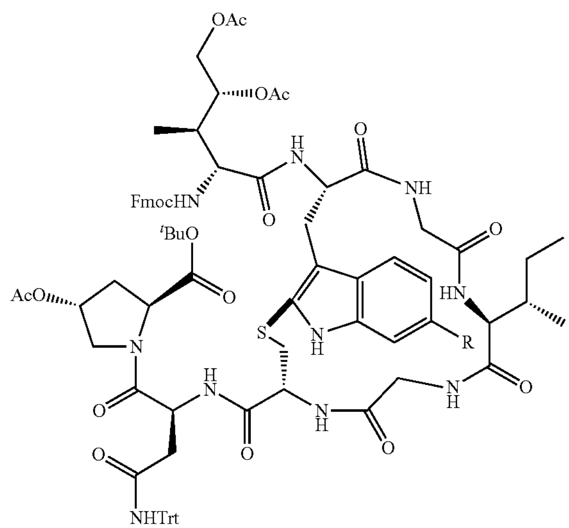
-continued
12
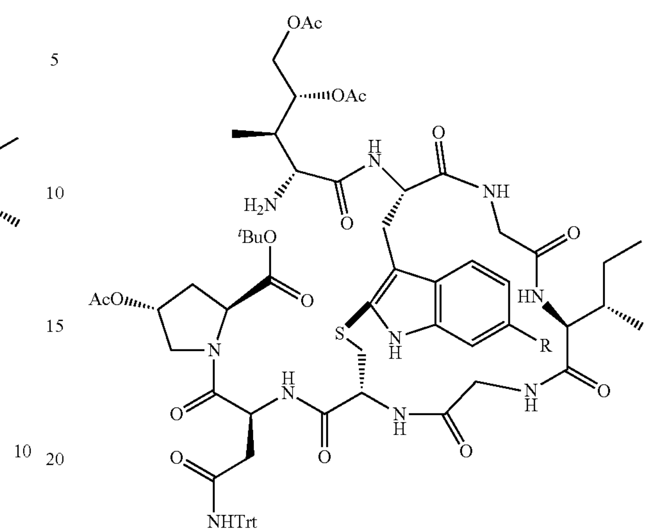
13
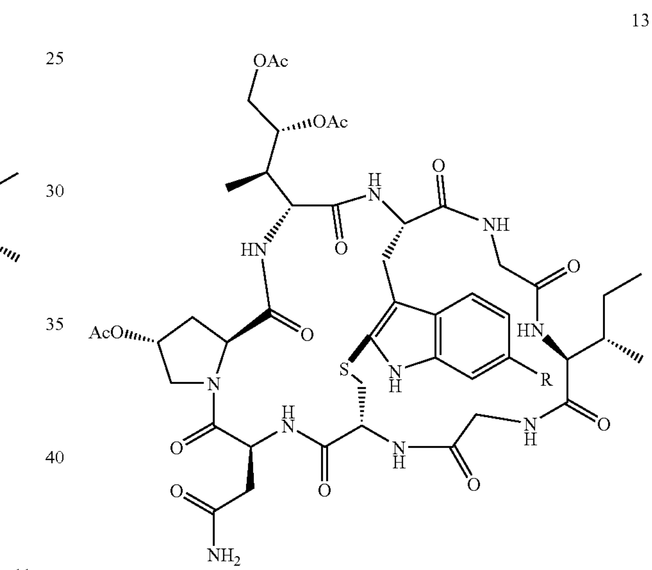
14
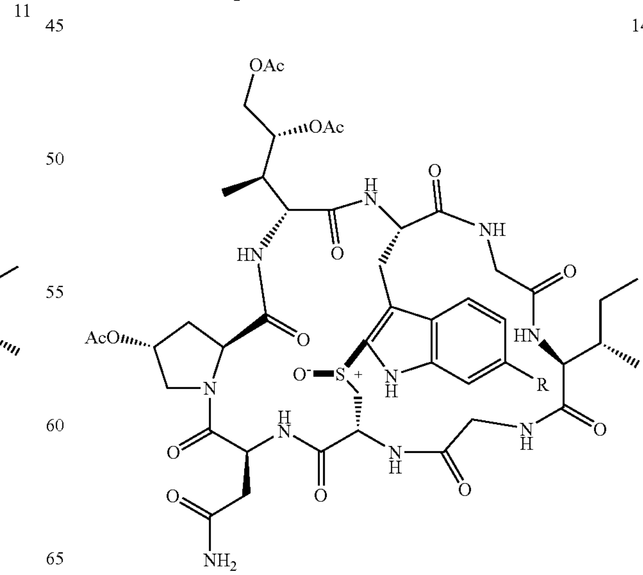
.

where R in the compounds 9 to 14 is selected from the group consisting of —H and —OBn.

The present disclosure further provides a method for preparing the intermediates, where the method of the intermediates is consistent with the method of the compounds 4 to 14, and will not be repeated here.

The present disclosure further provides use of the intermediates as described above in preparation of cyclic peptide toxin compounds.

The technical solutions of the present disclosure will be clearly and completely described below with reference to the examples of the present disclosure. Apparently, the examples described are merely some rather than all of the examples of the present disclosure. All other examples obtained by a person of ordinary skill in the art based on the examples of the present disclosure without creative efforts shall fall within the scope of the present disclosure.

Example 1 Synthesis of Compound 3

A principle was as follows:

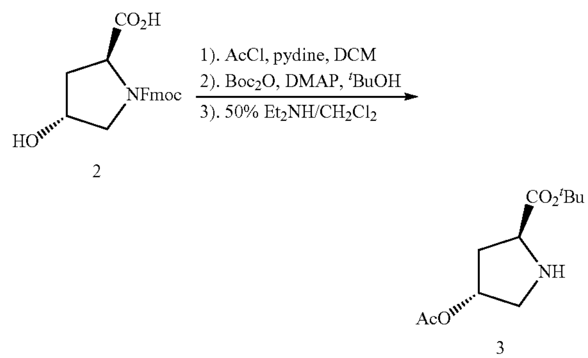

2

3

A 2,500 mL round-bottom flask was taken, and a magnetic stirring bar was placed in the 2,500 mL round-bottom flask. A compound 2 (N-Fmoc-4-hydroxyproline) (35.31 g, 100 mmol) was added to the 2,500 mL round-bottom flask, and 200 mL of dry DCM was added thereto and stirred to dissolve. A resulting mixed solution was stirred in an ice-water bath for 5 min. Pyridine (11.86 g, 150 mmol) was added thereto using a syringe and stirred for 5 min. Acetyl chloride (11.70 g, 150 mmol) was slowly added dropwise thereto using a syringe. A resulting mixed solution was placed in an ice-water bath for 30 min, and then subjected to a reaction at room temperature for 1 h. After the reaction was terminated, a resulting reaction solution was adjusted to a pH value of 2 with 1 N hydrochloric acid and then extracted three times with 500 mL of DCM. Resulting organic phases were combined and then dried over anhydrous sodium sulfate, and the DCM was removed under reduced pressure to obtain a crude product. The crude product was directly used in the next synthesis reaction step without further purification. The crude product was dissolved in 400 mL of TBA, and DMAP (1.84 g, 30 mol %) was added thereto. A resulting mixed solution was stirred at room temperature. 100 mL of a solution of $(Boc)_2O$ (43.62 g, 200 mmol) dissolved in TBA was added dropwise into a resulting reaction solution. A resulting mixed solution was subjected to a reaction at room temperature, where the reaction was monitored by TLC until the raw materials were consumed. After the reaction was completed, the solvent TBA was removed under reduced pressure to obtain a crude product. The crude product was dissolved in 150 mL of DCM, and 150 mL of DEA was added thereto to remove a protecting group Fmoc. The reaction was terminated by TLC monitoring until the raw materials were consumed. The mixed solution of DCM and DEA was removed under reduced pressure to obtain a crude product, which was then purified by 200-300 mesh silica gel column chromatography (a volume ratio of ethyl acetate/petroleum ether being 40% to 50%) to obtain 15.46 g of a yellow oily liquid, with a yield of 67.5%, $^1H$ NMR (600 MHz, DMSO) δ 5.07 (d, J=2.7 Hz, 1H), 3.65 (t, J=7.6 Hz, 1H), 3.15 (dd, J=12.0, 5.2 Hz, 1H), 2.76 (dd, J=12.0, 1.5 Hz, 1H), 2.00-1.98 (m, 5H), 1.40 (s, 9H). $^{13}C$ NMR (151 MHz, DMSO) δ 173.1, 170.1, 80.2, 75.0, 59.1, 52.2, 36.4, 27.6, 20.9. HRMS (ESI+) calcd (calculated). for $C_{11}H_{20}NO_4^+$ $(M+H)^+$: 230.1387; found: 230.1399.

Example 2 Synthesis of Compound 4

A principle was as follows:

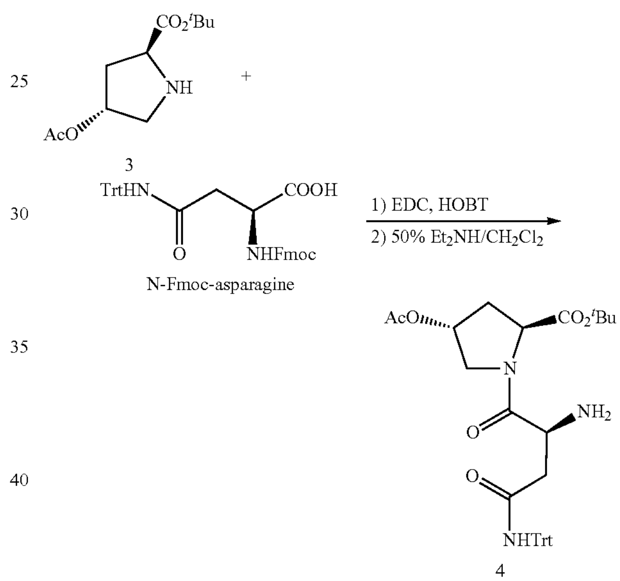

3

N-Fmoc-asparagine

4

A 2,500 mL round-bottom flask was taken, and a magnetic stirring bar was placed in the 2,500 mL round-bottom flask. A compound N-Fmoc-asparagine (65.60 g, 0.11 mol) was added to the 2,500 mL round-bottom flask, and 500 mL of dry DCM was added thereto and stirred to dissolve. A resulting mixed solution was placed in an ice-water bath for 5 min. EDC-HCl (12.70 g, 0.11 mol) and 1-hydroxybenzotriazole (14.90 g, 0.11 mol) were added thereto. A resulting mixed solution was placed in an ice-water bath for 30 min. Then the compound 3 (35.70 g, 0.1 mol) was added dropwise thereto. A resulting mixed solution was subjected to a reaction in an ice-water bath for 30 min. A reaction was conducted at room temperature overnight and monitored by TLC until the raw materials were consumed. Resulting organic phases were washed three times with saturated sodium bicarbonate, extracted three times with 1,000 mL of DCM, combined, washed with brine, then dried over anhydrous sodium sulfate, and filtered. The solvent was removed under reduced pressure to obtain a crude product. The unpurified crude product was directly used for the next deprotection group reaction. The crude product was dissolved in a 50 wt % solution of DEA in DCM. A resulting mixed solution was stirred at room temperature. A reaction was terminated after the raw materials were consumed as monitored by TLC. The solvent and DEA were removed under reduced pressure to obtain a crude product, which was then purified by 200-300 mesh silica gel column chromatography (a volume ratio of ethyl acetate/petroleum ether being 50% to 60%) to obtain 52.00 g of a white solid compound 4, with a yield of 89%, $^1H$ NMR (600 MHz, DMSO) δ 9.27 (s, 1H), 7.31-7.15 (m, 15H), 5.25 (s, 1H), 4.24 (t, J=8.1 Hz, 1H), 3.79 (dd, J=16.9, 11.3 Hz, 2H), 3.68 (dd, J=11.3, 3.8 Hz, 1H), 2.41 (dd, J=14.5, 10.9 Hz, 1H), 2.34-2.26 (m, 1H), 2.20 (d, J=14.7 Hz, 1H), 2.11-2.03 (m, 1H), 2.01 (s, 3H), 1.89 (d, J=10.8 Hz, 2H), 1.38 (s, 9H). $^{13}C$ NMR (151 MHz, DMSO) δ 173.1, 170.3, 169.9, 169.6, 145.0, 128.5, 127.4, 126.3, 80.6, 72.7, 69.4, 58.2, 51.5, 49.9, 40.8, 33.9, 27.5, 20.9. HRMS (ESI+) calcd. for $C_{34}H_{40}N_3O_6^+$ $(M+H)^+$: 586.2912; found: 586.2896.

Example 3 Synthesis of Compound 5

A principle was as follows:

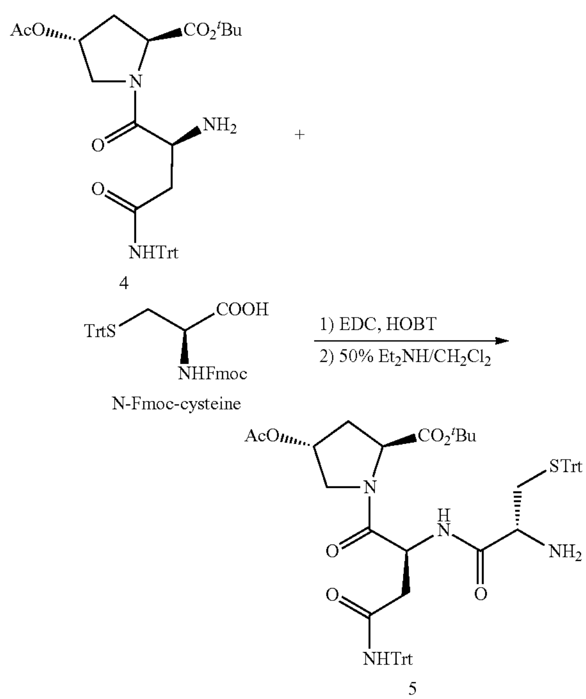

4

N-Fmoc-cysteine

5

A 2,500 mL round-bottom flask was taken, and a magnetic stirring bar was placed in the 2,500 mL round-bottom flask. A compound N-Fmoc-cysteine (64.40 g, 0.11 mol) was added to the 2,500 mL round-bottom flask, and 500 mL of dry DCM was added thereto and stirred to dissolve. A resulting mixed solution was subjected to a reaction in an ice-water bath for 5 min. EDC-HCl (12.70 g, 0.11 mol) and 1-hydroxybenzotriazole (14.90 g, 0.11 mol) were added thereto. A resulting mixed solution was subjected to a reaction in an ice-water bath for 30 min. Then the compound 4 (70.70 mg, 0.11 mol) was added dropwise thereto. A resulting mixed solution was subjected to a reaction in an ice-water bath for 30 min. A reaction was conducted at room temperature overnight and monitored by TLC until the raw materials were consumed. Resulting organic phases were washed with saturated sodium bicarbonate, extracted three times with 1,000 mL of DCM, combined, washed with brine, then dried over anhydrous sodium sulfate, and filtered. The solvent was removed under reduced pressure to obtain a crude product. The unpurified crude product was directly used for the next deprotection. The crude product was dissolved in a 50 wt % solution of DEA in DCM. A resulting mixed solution was stirred at room temperature. A reaction was terminated after the raw materials were consumed as monitored by TLC. The solvent and DEA were removed under reduced pressure to obtain a crude product, which was then purified by 200-300 mesh silica gel column chromatography (a volume ratio of ethyl acetate/petroleum ether being 75% to 80%) to obtain 76.30 g of a white solid compound 5, with a yield of 82%, $^1H$ NMR (600 MHz, DMSO) δ 8.73 (s, 1H), 8.25 (d, J=7.8 Hz, 1H), 7.34-7.29 (m, 12H), 7.23 (dd, J=15.4, 7.2 Hz, 10H), 7.16 (d, J=7.4 Hz, 8H), 5.20 (s, 1H), 4.65 (dd, J=13.0, 8.0 Hz, 1H), 4.21 (t, J=8.1 Hz, 1H), 3.74 (dt, J=11.6, 7.9 Hz, 2H), 3.13 (dd, J=7.7, 5.0 Hz, 1H), 2.65 (dd, J=14.8, 8.9 Hz, 1H), 2.50-2.48 (m, 2H), 2.25 (ddd, J=20.0, 11.6, 7.1 Hz, 2H), 2.05 (ddd, J=13.4, 7.8, 5.3 Hz, 1H), 1.93 (s, 3H), 1.70 (s, 2H), 1.39 (s, 9H). $^{13}C$ NMR (151 MHz, DMSO) δ 172.8, 170.1, 169.9, 169.6, 168.3, 144.7, 144.5, 129.1, 128.5, 127.9, 127.4, 126.7, 126.3, 80.7, 72.4, 69.5, 65.9, 58.1, 53.8, 51.7, 47.9, 38.0, 37.1, 33.9, 27.5, 20.8. HRMS (ESI+) calcd, for $C_{34}H_{40}N_3O_6^+$ $(M+H)^+$: 931.4099; found: 931.4084.

Example 4: Synthesis of Compound 6

A principle was as follows:

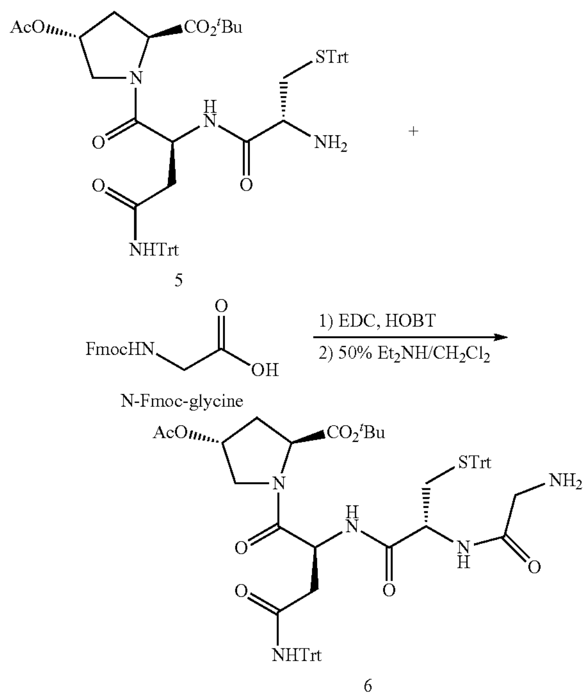

5

N-Fmoc-glycine

6

A 2,500 mL round-bottom flask was taken, and a magnetic stirring bar was placed in the 2,500 mL round-bottom flask. A compound N-Fmoc-glycine (32.70 g, 0.11 mol) was added to the 2,500 mL round-bottom flask, and 500 mL of dry DCM was added thereto and stirred to dissolve. A resulting mixed solution was subjected to a reaction in an ice-water bath for 5 min. EDC-HCl (12.70 g, 0.11 mol) and 1-hydroxybenzotriazole (14.90 g, 0.11 mol) were added thereto. A resulting mixture was subjected to a reaction in an ice-water bath for 30 min. Then the compound 5 (108.70 g, 0.11 mol) was added dropwise thereto. A resulting mixture was subjected to a reaction in an ice-water bath for 30 min. A reaction was conducted at room temperature overnight and monitored by TLC until the raw materials were consumed. Resulting organic phases were washed with saturated sodium bicarbonate, extracted three times with 1,000 mL of DCM, combined, washed with brine, then dried over anhydrous sodium sulfate, and filtered. The solvent was removed under reduced pressure to obtain a crude product. The unpurified crude product was directly used for the next deprotection group reaction. The crude product was dissolved in a 50 wt % solution of DEA in DCM. A resulting mixed solution was stirred at room temperature. A reaction was terminated after the raw materials were consumed as monitored by TLC. The solvent and DEA were removed under reduced pressure to obtain a crude product, which was then purified by 200-300 mesh silica gel column chromatography (a volume ratio of methanol/DCM being 0% to 0.5%) to obtain 68.10 g of a white solid compound 6, with a yield of 69%, $^1H$ NMR (600 MHz, DMSO) δ 8.66 (s, 1H), 8.55 (d, J=7.7 Hz, 1H), 8.13 (s, 1H), 7.39-7.29 (m, 12H), 7.28-7.21 (m, 10H), 7.20-7.13 (m, 8H), 5.21 (s, 1H), 4.73 (d, J=5.6 Hz, 1H), 4.53 (t, J=5.7 Hz, 1H), 4.23 (t, J=8.0 Hz, 1H), 3.75 (dt, J=11.5, 8.1 Hz, 2H), 3.13-3.05 (m, 2H), 2.63 (dd, J=15.2, 8.5 Hz, 1H), 2.56 (dd, J=15.1, 4.9 Hz, 1H), 2.40 (d, J=5.9 Hz, 2H), 2.28-2.22 (m, 1H), 2.10-2.03 (m, 1H), 1.93 (s, 3H), 1.86 (s, 2H), 1.41 (s, 9H). $^{13}C$ NMR (151 MHz, DMSO) δ 172.4, 170.1, 170.0, 169.4, 169.3, 168.2, 144.7, 144.272, 129.1, 128.5, 128.0, 127.4, 126.7, 126.3, 80.6, 72.4, 69.5, 65.7, 58.2, 51.7, 50.2, 47.9, 44.5, 39.5, 37.8, 34.5, 33.8, 27.6, 20.7. HRMS (ESI+) calcd. for $C_{58}H_{62}N_5O_8S+$ $(M+H)^+$: 988.4314; found: 988.4307.

Example 5: Synthesis of Compound 7

A principle was as follows:

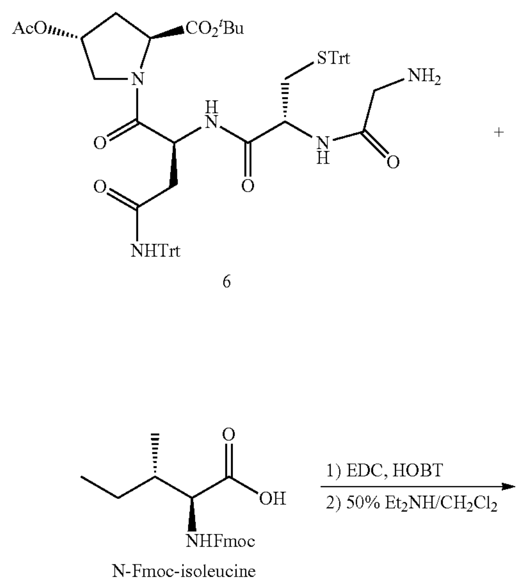

6

N-Fmoc-isoleucine

-continued

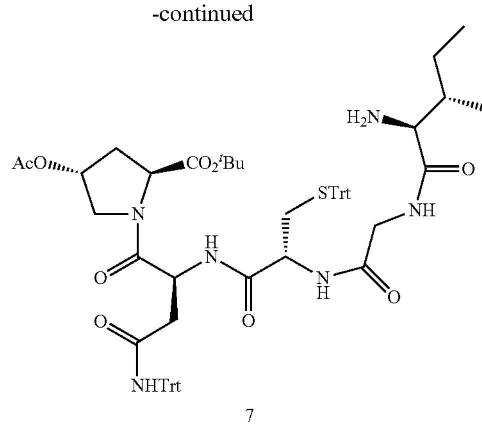

7

A 2,500 mL round-bottom flask was taken, and a magnetic stirring bar was placed in the 2,500 mL round-bottom flask. A compound N-Fmoc-isoleucine (35.30 g, 0.11 mol) was added to the 2,500 mL round-bottom flask, and 500 mL of dry DCM was added thereto and stirred to dissolve. A resulting mixed solution was subjected to a reaction in an ice-water bath for 5 min. EDC-HCl (12.70 g, 0.11 mol) and 1-hydroxybenzotriazole (14.90 g, 0.11 mol) were added thereto. A resulting mixture was subjected to a reaction in an ice-water bath for 30 min. Then the compound 6 (98.70 g, 0.10 mol) was added dropwise thereto. A resulting mixture was subjected to a reaction in an ice-water bath for 30 min. A reaction was conducted at room temperature overnight and monitored by TLC until the raw materials were consumed. Resulting organic phases were washed with saturated sodium bicarbonate, extracted three times with 1,000 mL of DCM, combined, washed with brine, then dried over anhydrous sodium sulfate, and filtered. The solvent was removed under reduced pressure to obtain a crude product. The unpurified crude product was directly used for the next deprotection group reaction. The crude product was dissolved in a 50 wt % solution of DEA in DCM. A resulting mixed solution was stirred at room temperature. A reaction was terminated after the raw materials were consumed as monitored by TLC. The solvent and DEA were removed under reduced pressure to obtain a crude product, which was then purified by 200-300 mesh silica gel column chromatography (a volume ratio of methanol/DCM being 0% to 1%) to obtain 80.30 g of a white solid compound 7, with a yield of 73%, $^1H$ NMR (600 MHz, DMSO) δ 8.67 (s, 1H), 8.45 (d, J=7.1 Hz, 1H), 8.16 (s, 1H), 8.10 (d, J=7.9 Hz, 1H), 7.33-7.30 (m, 12H), 7.25-7.23 (m, 10H), 7.18 (d, J=6.7 Hz, 8H), 5.19 (s, 1H), 4.72 (d, J=6.4 Hz, 1H), 4.48 (d, J=6.4 Hz, 1H), 4.21 (t, J=7.6 Hz, 1H), 3.76-3.73 (m, 4H), 3.36 (s, 1H), 3.06 (d, J=4.2 Hz, 1H), 2.68-2.54 (m, 2H), 2.42 (d, J=5.6 Hz, 1H), 2.38-2.28 (m, 1H), 2.23-2.21 (m, 1H), 2.11-2.01 (m, 1H), 1.91 (s, 3H), 1.69 (d, J=30.6 Hz, 2H), 1.41 (s, 9H), 1.12-1.02 (m, 1H), 0.85 (d, J=6.4 Hz, 3H), 0.79 (t, J=7.0 Hz, 3H). $^{13}C$ NMR (151 MHz, DMSO) δ 174.9, 170.1, 169.9, 169.3, 169.1, 168.6, 168.3, 144.6, 144.2, 129.0, 128.5, 127.9, 127.4, 126.6, 126.3, 80.6, 72.2, 69.5, 65.7, 59.3, 58.1, 51.6, 50.9, 47.9, 41.9, 38.1, 34.1, 33.8, 27.6, 23.7, 20.7, 15.8, 11.6. HRMS (ESI+) calcd, for $C_{64}H_{73}N_6O_9S^+$ $(M+H)^+$: 1101.5104; found: 1101.5122.

Example 6: Synthesis of Compound 8

A principle was as follows:

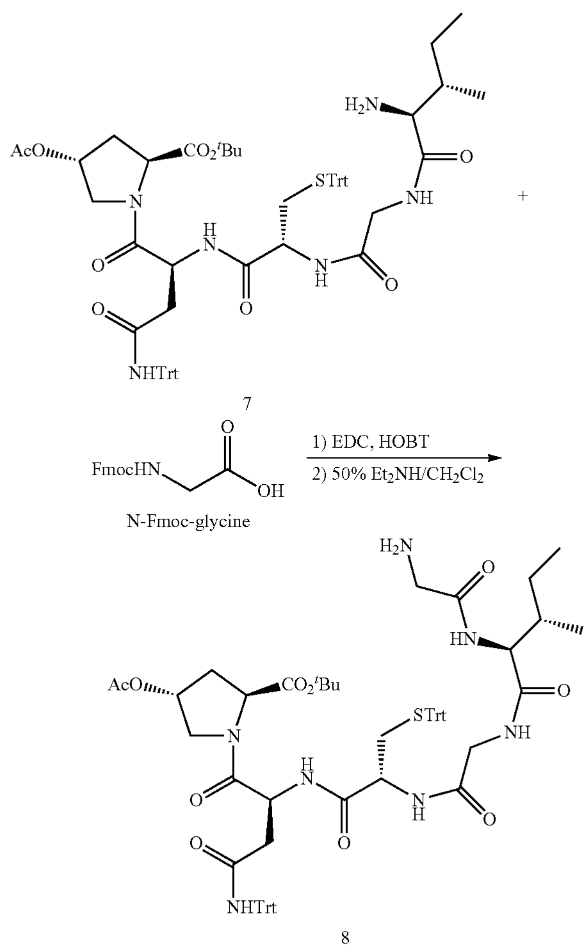

7

N-Fmoc-glycine

8

A 2,500 mL round-bottom flask was taken, and a magnetic stirring bar was placed in the 2,500 mL round-bottom flask. A compound N-Fmoc-glycine (32.60 g, 0.11 mol) was added to the 2,500 mL round-bottom flask, and 500 mL of dry DCM was added thereto and stirred to dissolve. A resulting mixed solution was subjected to a reaction in an ice-water bath for 5 min. EDC-HCl (12.70 g, 0.11 mol) and 1-hydroxybenzotriazole (14.90 g, 0.11 mol) were added thereto. A resulting mixture was subjected to a reaction in an ice-water bath for 30 min. Then the compound 7 (110.00 g, 0.10 mol) was added dropwise thereto. A resulting mixture was subjected to a reaction in an ice-water bath for 30 min. A reaction was conducted at room temperature overnight and monitored by TLC until the raw materials were consumed. Resulting organic phases were washed with saturated sodium bicarbonate, extracted three times with 1,000 mL of DCM, combined, washed with brine, then dried over anhydrous sodium sulfate, and filtered. The solvent was removed under reduced pressure to obtain a crude product. The unpurified crude product was directly used for the next deprotection group reaction. The crude product was dissolved in a 50 wt % solution of DEA in DCM. A resulting mixed solution was stirred at room temperature. A reaction was terminated after the raw materials were consumed as monitored by TLC. The solvent and DEA were removed under reduced pressure to obtain a crude product, which was then purified by 200-300 mesh silica gel column chromatography (a volume ratio of methanol/DCM being 0% to 1.5%) to obtain 70.60 g of a white solid compound 8, with a yield of 61%, $^1H$ NMR (600 MHz, DMSO) δ 8.68 (s, 1H), 8.46 (d, J=7.4 Hz, 1H), 8.32 (d, J=5.3 Hz, 1H), 8.07 (d, J=8.0 Hz, 1H), 7.97 (s, 1H), 7.35-7.28 (m, 12H), 7.25-7.23 (m, 10H), 7.18 (d, J=7.7 Hz, 8H), 5.19 (s, 1H), 4.72 (dd, J=13.7, 7.0 Hz, 1H), 4.46 (dd, J=13.8, 7.0 Hz, 1H), 4.26 (s, 1H), 4.21 (t, J=7.8 Hz, 1H), 3.79-3.73 (m, 4H), 3.45-3.30 (m, 1H), 3.11 (d, J=6.6 Hz, 2H), 2.65 (dd, J=15.1, 5.1 Hz, 1H), 2.56 (dd, J=15.2, 7.4 Hz, 1H), 2.50 (s, 1H), 2.40 (dd, J=11.0, 5.1 Hz, 1H), 2.37-2.28 (m, 1H), 2.22 (t, J=9.3 Hz, 1H), 2.10-2.03 (m, 1H), 1.98 (d, J=8.6 Hz, 1H), 1.90 (d, J=6.2 Hz, 3H), 1.76 (t, J=14.7 Hz, 1H), 1.50-1.43 (m, 1H), 1.41 (s, 9H), 1.10-1.00 (m, 1H), 0.84 (d, J=6.7 Hz, 3H), 0.81 (t, J=7.3 Hz, 3H). $^{13}C$ NMR (151 MHz, DMSO) δ 172.7, 171.4, 170.1, 169.9, 169.4, 169.7, 168.4, 168.3, 144.7, 144.2, 129.1, 128.6, 128.5, 128.0, 127.4, 126.7, 126.3, 80.6, 72.3, 69.5, 65.7, 58.1, 56.5, 51.7, 51.0, 47.8, 44.5, 41.8, 37.9, 37.1, 34.2, 33.8, 27.6, 24.3, 20.7, 15.4, 11.2. HRMS (ESI+) calcd, for $C_{66}H_{76}N_7O_{10}S^+$ $(M+H)^+$: 1158.5369; found: 1158.5354.

Example 7 Synthesis of Compounds 9a and 9b

A principle was as follows:

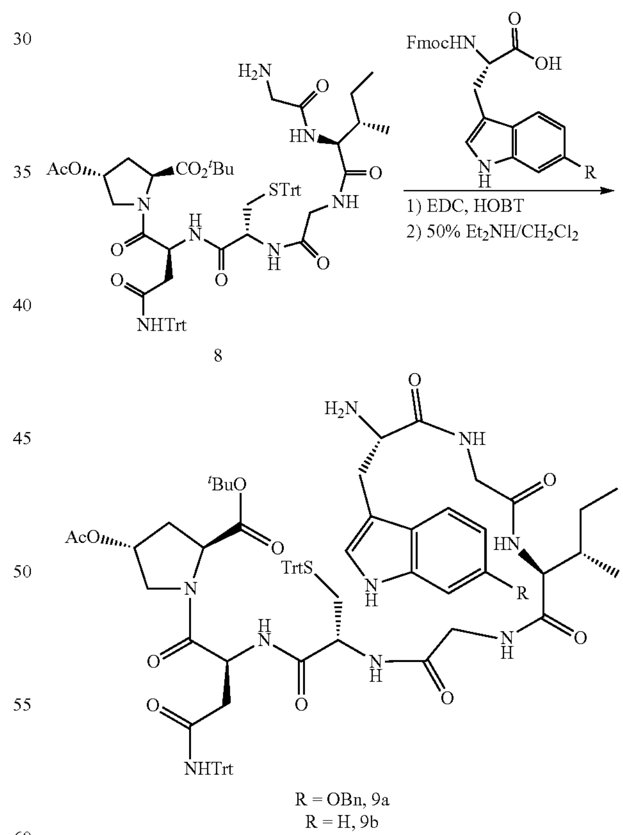

8

R = OBn, 9a
R = H, 9b

A 2,500 mL round-bottom flask was taken, and a magnetic stirring bar was placed in the 2,500 mL round-bottom flask. A compound N-Fmoc-6-benzyloxytryptophan (68.90 g, 0.10 mol) was added to the 2,500 mL round-bottom flask, and 500 mL of dry DCM was added thereto and stirred to dissolve. A resulting mixed solution was subjected to a reaction in an ice-water bath for 5 min. EDC-HCl (12.70 g, 0.11 mol) and 1-hydroxybenzotriazole (14.90 g, 0.11 mol) were added thereto. A resulting mixture was subjected to a reaction in an ice-water bath for 30 min. Then the compound 8 (143.80 g, 0.11 mol) was added dropwise thereto. A resulting mixture was subjected to a reaction in an ice-water bath for 30 min. A reaction was conducted at room temperature overnight and monitored by TLC until the raw materials were consumed. Resulting organic phases were washed with saturated sodium bicarbonate, extracted three times with 1,000 mL of DCM, combined, washed with brine, then dried over anhydrous sodium sulfate, and filtered. The solvent was removed under reduced pressure to obtain a crude product. The unpurified crude product was directly used for the next deprotection group reaction. The crude product was dissolved in a 50 wt % solution of DEA in DCM. A resulting mixed solution was stirred at room temperature. A reaction was terminated after the raw materials were consumed as monitored by TLC. The solvent and DEA were removed under reduced pressure to obtain a crude product, which was then purified by 200-300 mesh silica gel column chromatography (a volume ratio of methanol/DCM being 0% to 2%) to obtain 100.00 g of a white solid compound 9a, with a yield of 69%, $^1$H NMR (600 MHz, DMSO) § 10.65 (s, 1H), 8.64 (s, 1H), 8.46 (d, J=7.4 Hz, 1H), 8.24 (d, J=5.5 Hz, 1H), 8.18 (s, 1H), 8.02 (d, J=7.9 Hz, 1H), 7.92 (d, J=8.5 Hz, 1H), 7.46 (d, J=7.4 Hz, 2H), 7.42 (d, J=8.6 Hz, 1H), 7.38 (t, J=7.5 Hz, 2H), 7.32-7.28 (m, 12H), 7.24-7.22 (m, 10H), 7.18-7.15 (m, 8H), 7.10 (d, J=7.8 Hz, 1H), 7.04 (s, 1H), 6.91 (s, 1H), 6.72 (d, J=8.6 Hz, 1H), 5.17 (s, 1H), 5.10-5.08 (m, 2H), 4.73-4.67 (m, 1H), 4.48-4.42 (m, 1H), 4.24 (t, J=7.7 Hz, 1H), 4.19 (t, J=7.9 Hz, 1H), 3.82-3.78 (m, 1H), 3.78-3.74 (m, 2H), 3.70 (s, 2H), 3.46 (dd, J=8.6, 4.1 Hz, 1H), 3.07 (dd, J=14.1, 3.7 Hz, 1H), 2.72-2.58 (m, 2H), 2.56-2.52 (m, 1H), 2.37 (dd, J=11.1, 5.1 Hz, 1H), 2.33-2.27 (m, 1H), 2.25-2.15 (m, 1H), 2.05 (dd, J=13.6, 6.6 Hz, 1H), 1.88 (s, 3H), 1.73 (s, 2H), 1.45 (s, 1H), 1.40 (s, 9H), 1.12-1.02 (m, 1H), 0.83 (d, J=6.7 Hz, 3H), 0.78 (t, J=7.2 Hz, 3H). $^{13}$C NMR (151 MHz, DMSO) δ 174.9, 171.2, 170.1, 169.9, 169.3, 169.1, 168.7, 168.3, 168.2, 154.4, 144.6, 144.2, 137.7, 136.8, 129.0, 128.5, 128.3, 127.9, 127.5, 127.4, 126.6, 126.3, 122.5, 118.9, 110.6, 109.1, 96.0, 80.6, 72.2, 69.5, 65.7, 58.1, 56.9, 55.2, 51.6, 50.9, 47.8, 41.9, 41.8, 37.9, 36.7, 34.2, 33.8, 30.9, 27.6, 24.2, 20.7, 15.3, 11.1. HRMS (ESI+) calcd. for $C_{84}H_{92}N_9O_{12}S^+$ $(M+H)^+$: 1450.6581; found: 1450.6591.

Referring to the synthesis method of the compound 9a, the compound 8 (143.80 g, 0.11 mol) was reacted with N-Fmoc-tryptophan (42.60 g, 0.10 mol) and the Fmoc protecting group was removed to obtain 104.80 g of a white solid compound 9b, with a yield of 78%, $^1$H NMR (600 MHz, DMSO) δ 10.87 (s, 1H), 8.67 (s, 1H), 8.49 (d, J=6.8 Hz, 1H), 8.28 (s, 1H), 8.22 (s, 1H), 8.06 (d, J=7.5 Hz, 1H), 7.96 (d, J=8.1 Hz, 1H), 7.56 (d, J=7.6 Hz, 1H), 7.36-7.31 (m, 13H), 7.24-7.23 (m, 8H), 7.18 (d, J=6.9 Hz, 10H), 7.12 (d, J=7.4 Hz, 1H), 7.07 (t, J=7.2 Hz, 1H), 6.97 (t, J=7.1 Hz, 1H), 5.18 (s, 1H), 4.73 (d, J=6.4 Hz, 1H), 4.48 (d, J=6.4 Hz, 1H), 4.26 (t, J=7.3 Hz, 1H), 4.21 (t, J=7.7 Hz, 1H), 3.82-3.73 (m, 5H), 3.54-3.47 (m, 1H), 3.38 (s, 2H), 3.19-3.08 (m, 1H), 2.74 (dd, J=13.8, 9.0 Hz, 1H), 2.64 (d, J=10.5 Hz, 1H), 2.56 (dd, J=14.5, 7.0 Hz, 1H), 2.39 (d, J=5.8 Hz, 1H), 2.37-2.27 (m, 1H), 2.22 (s, 1H), 2.11-2.02 (m, 1H), 1.94-1.84 (m, 3H), 1.76 (s, 2H), 1.47 (s, 1H), 1.41 (s, 9H), 1.15-1.04 (m, 1H), 0.85 (d, J=6.2 Hz, 3H), 0.80 (t, J=7.0 Hz, 3H). $^{13}$C NMR (151 MHz, DMSO) δ 174.9, 171.3, 170.1, 169.9, 169.4, 169.2, 168.8, 168.3, 168.2, 144.7, 144.2, 136.3, 129.1, 128.6, 128.5, 128.0, 127.4, 126.7, 126.3, 123.8, 120.9, 118.4, 118.3, 111.3, 110.7, 80.7, 72.3, 69.5, 65.7, 58.1, 56.9, 55.3, 51.7, 50.9, 47.8, 41.9, 41.8, 37.9, 36.8, 34.3, 33.8, 30.9, 27.6, 24.2, 20.7, 15.4, 11.2. HRMS (ESI+) calcd. for $C_{77}H_{86}N_9O_{11}S^+$ $(M+H)^+$: 1344.6162; found: 1344.6189.

Example 8 Synthesis of Compounds 10a and 10b

A principle was as follows:

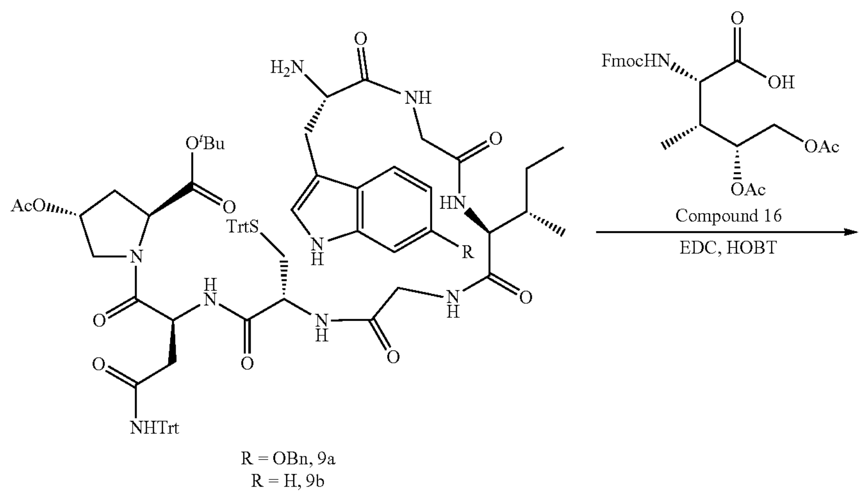

R = OBn, 9a
R = H, 9b

-continued

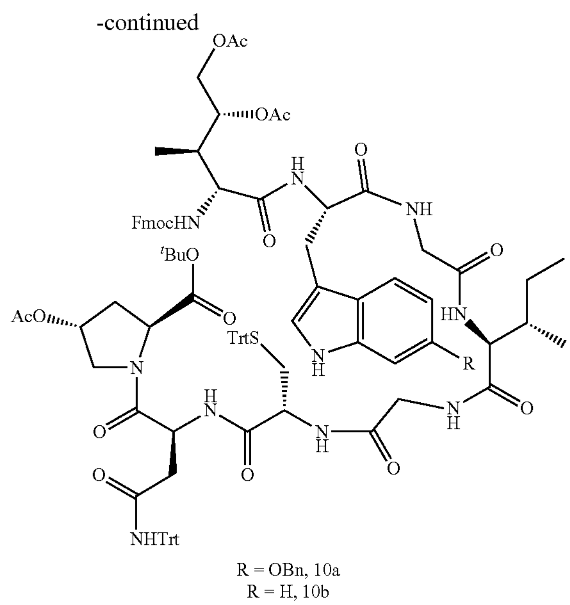

R = OBn, 10a
R = H, 10b

A 2,500 mL round-bottom flask was taken, and a magnetic stirring bar was placed in the 2,500 mL round-bottom flask. A compound 16 (2S,3R,4R)-4,5-dihydroxyisoleucine derivative (46.90 g, 0.10 mol) was added to the 2,500 mL round-bottom flask, and 500 mL of dry DCM was added thereto and stirred to dissolve. A resulting mixed solution was subjected to a reaction in an ice-water bath for 5 min. EDC-HCl (12.70 g, 0.11 mol) and 1-hydroxybenzotriazole (14.90 g, 0.11 mol) were added thereto. A resulting mixture was subjected to a reaction in an ice-water bath for 30 min. Then the compound 9a (183.10 g, 0.11 mol) was added dropwise thereto. A resulting mixture was subjected to a reaction in an ice-water bath for 30 min. A reaction was conducted at room temperature overnight and monitored by TLC until the raw materials were consumed. Resulting organic phases were washed with saturated sodium bicarbonate, extracted three times with 1,000 mL of DCM, combined, washed with brine, then dried over anhydrous sodium sulfate, and filtered. The solvent was removed under reduced pressure to obtain a crude product. The crude product was purified by 200-300 mesh silica gel column chromatography (a volume ratio of methanol/DCM being 0% to 2%) to obtain 152.00 g of a white solid compound 10a, with a yield of 80%, $^{1}$H NMR (600 MHz, DMSO) δ 10.66 (s, 1H), 8.68 (s, 1H), 8.51 (s, 1H), 8.33 (s, 1H), 8.28 (s, 1H), 8.16-8.05 (m, 1H), 8.07-8.03 (m, 2H), 7.90-7.89 (m, 3H), 7.75 (dd, J=13.3, 7.3 Hz, 2H), 7.58 (d, J=9.0 Hz, 1H), 7.55-7.49 (m, 2H), 7.47 (d, J=7.2 Hz, 2H), 7.45-7.37 (m, 5H), 7.35-7.30 (m, 13H), 7.26-7.24 (d, J=6.7 Hz, 10H), 7.20 (d, J=7.0 Hz, 8H), 7.14 (d, J=7.5 Hz, 1H), 7.10 (s, 1H), 6.94 (s, 1H), 6.76 (d, J=8.2 Hz, 1H), 5.20 (s, 1H), 5.11-5.08 (d, J=16.4 Hz, 3H), 4.84-4.74 (m, 2H), 4.71 (d, J=5.5 Hz, 1H), 4.55-4.46 (m, 2H), 4.38 (dd, J=24.5, 10.2 Hz, 2H), 4.31 (s, 1H), 4.24 (dt, J=14.8, 7.4 Hz, 2H), 4.19-4.11 (m, 1H), 4.04 (d, J=7.6 Hz, 1H), 3.81 (s, 4H), 3.75 (s, 2H), 3.41 (s, 1H), 3.17 (d, J=11.0 Hz, 1H), 3.05 (s, 1H), 2.67 (d, J=10.7 Hz, 1H), 2.60 (s, 1H), 2.42 (s, 1H), 2.35 (s, 1H), 2.23 (s, 1H), 2.13-2.04 (m, 1H), 1.98 (dd, J=16.9, 6.9 Hz, 6H), 1.91 (d, J=8.7 Hz, 3H), 1.79 (s, 1H), 1.47 (d, J=26.7 Hz, 1H), 1.42 (s, 9H), 1.14 (d, J=26.1 Hz, 1H), 0.87 (s, 3H), 0.80 (t, J=20.4 Hz, 3H), 0.76 (d, J=5.5 Hz, 3H). $^{13}$C NMR (151 MHz, DMSO) δ 171.6, 171.3, 170.5, 170.2, 170.1, 169.9, 169.7, 169.4, 169.2, 168.5, 168.4, 168.3, 156.3, 154.5, 144.7, 144.3, 144.0, 143.7, 140.7, 140.6, 137.7, 136.7, 129.1, 128.6, 128.5, 128.3, 128.0, 127.7, 127.6, 127.4, 127.2, 126.7, 126.3, 125.6, 125.3, 122.5, 122.1, 120.1, 119.0, 109.8, 109.1, 95.9, 80.7, 72.3, 71.6, 69.6, 69.5, 66.2, 65.7, 62.9, 58.1, 56.9, 54.9, 54.7, 53.5, 51.7, 50.9, 47.9, 46.7, 42.1, 41.8, 39.5, 37.9, 36.8, 35.3, 34.3, 33.9, 27.6, 27.5, 24.2, 20.8, 20.7, 20.6, 15.4, 11.2, 10.3. HRMS (ESI+) calcd, for $C_{109}H_{116}N_{10}NaO_{19}S^+$ (M+Na)$^+$: 1923.8031; found: 1923.8068.

Referring to the synthesis method of the compound 10a, the compound 9b (180.00 g, 0.11 mol) was reacted with compound 16 (2S,3R,4R)-4,5-dihydroxyisoleucine derivative (46.90 g, 0.10 mol) and the Fmoc protecting group was removed to obtain 147.20 g of a white solid compound 10b, with a yield of 82%, $^{1}$H NMR (600 MHz, DMSO) δ 10.86 (s, 1H), 8.70 (s, 1H), 8:53 (s, 1H), 8.36 (s, 1H), 8.30 (s, 1H), 8.09 (s, 1H), 7.90 (d, J=6.5 Hz, 3H), 7.77 (dd, J=16.4, 6.9 Hz, 2H), 7.67 (d, J=7.2 Hz, 1H), 7.60 (d, J=8.0 Hz, 1H), 7.43 (s, 2H), 7.34 (s, 14H), 7.28-7.19 (m, 20H), 7.08 (d, J=6.8 Hz, 1H), 7.01 (s, 1H), 5.74 (s, 2H), 5.22 (s, 1H), 4.86-4.69 (m, 3H), 4.53 (s, 2H), 4.42 (d, J=11.0 Hz, 2H), 4.33 (s, 1H), 4.26 (d, J=7.4 Hz, 2H), 4.17 (s, 1H), 4.05 (d, J=7.6 Hz, 1H), 3.81 (d, J=33.7 Hz, 6H), 3.44 (s, 1H), 3.24 (d, J=10.3 Hz, 1H), 3.12 (s, 1H), 2.66 (d, J=39.3 Hz, 2H), 2.57-2.50 (m, 1H), 2.42 (d, J=46.2 Hz, 2H), 2.24 (s, 1H), 2.08 (s, 1H), 2.00 (d, J=11.4 Hz, 6H), 1.91 (s, 3H), 1.82 (s, 1H), 1.51 (s, 1H), 1.43 (s, 9H), 1.14 (s, 1H), 0.82 (m, 9H). $^{13}$C NMR (151 MHz, DMSO) δ 171.7, 171.3, 170.6, 170.2, 170.1, 169.9, 169.7, 169.4, 169.2, 168.6, 168.4, 168.3, 156.3, 144.7, 144.3, 144.1, 143.7, 140.8, 140.7, 136.2, 129.1, 128.6, 128.0, 127.7, 127.6, 127.4, 127.2, 126.7, 126.4, 125.6, 125.3, 123.7, 120.8, 120.1, 118.4, 118.2, 111.3, 109.9, 80.7, 72.3, 71.6, 69.6, 66.2, 65.8, 63.0, 58.2, 56.9, 54.9, 54.7, 53.5, 51.7, 51.0, 47.9, 46.7, 42.2, 41.9, 39.5, 38.0, 36.8, 35.4, 34.3, 33.9, 28.0, 27.6, 24.3, 20.8, 20.7, 20.6, 15.4, 11.2, 10.4. HRMS (ESI+) calcd, for $C_{102}H_{110}N_{10}NaO_{18}S^+$ (M+Na)$^+$: 1817.7612; found: 1817.7625.

Example 9: Synthesis of Compounds 11a and 11b

A principle was as follows:

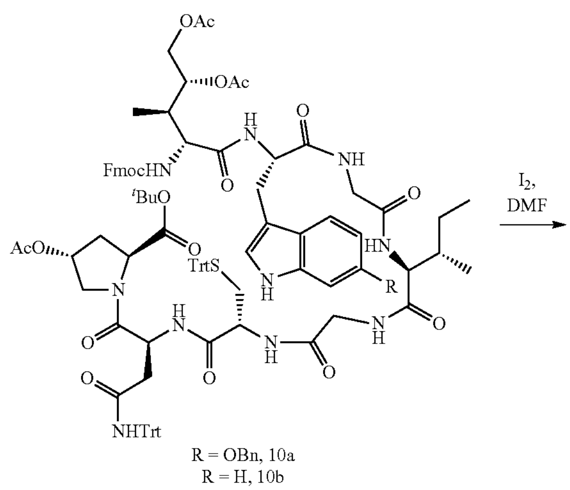

R = OBn, 10a
R = H, 10b

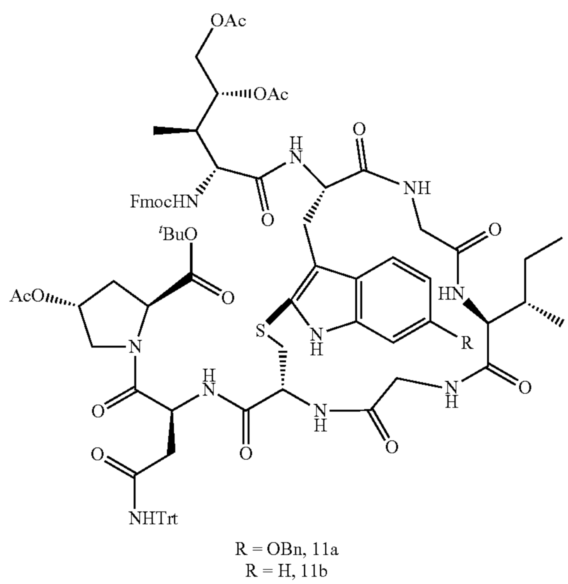

R = OBn, 11a
R = H, 11b

A 2,500 mL round-bottom flask was taken, and a magnetic stirring bar was placed in the 2,500 mL round-bottom flask, and gas therein was replaced three times using the Schlenk technique. Under $N_2$ atmosphere, the compound 10a (57.00 g, 0.03 mol) was added to the 2,500 mL round-bottom flask, and 500 mL of dry DMF was added thereto and stirred to dissolve. A resulting mixed solution was stirred at room temperature. A 2 mg/mL iodine solution in DMF was prepared and 4 equiv of the iodine solution was slowly added dropwise into the reaction flask using a syringe. A reaction was conducted at room temperature for 2 h. After the reaction was completed, an excess of sodium thiosulfate solution was added to the system reaction to quench the reaction. DMF was removed under reduced pressure. Resulting organic phases were extracted three times with 2,000 mL of ethyl acetate, combined, washed with brine, and then dried over anhydrous sodium sulfate, and filtered. The solvent was removed under reduced pressure to obtain a crude product. The crude product was purified by 200-300 mesh silica gel column chromatography (a volume ratio of methanol/DCM being 0% to 2%) to obtain 30.60 g of a white solid compound 11a, with a yield of 62%, $^1$H NMR (600 MHz, DMSO) δ 11.06 (d, J=49.8 Hz, 1H), 8.63 (s, 1H), 8.40 (s, 1H), 8.28 (d, J=45.1 Hz, 1H), 8.18-7.98 (m, 3H), 7.89 (s, 2H), 7.74-7.74 (m, 2H), 7.65-7.60 (m, 1H), 7.52-7.32 (m, 10H), 7.26-7.24 (m, 6H), 7.16 (t, J=13.4 Hz, 9H), 6.85 (s, 1H), 6.77 (d, J=9.1 Hz, 1H), 5.20 (s, 1H), 5.13-5.09 (m, 2H), 4.77 (s, 1H), 4.69 (s, 1H), 4.48-4.26 (m, 3H), 4.25-4.21 (m, 2H), 4.17-4.09 (m, 1H), 4.03 (s, 2H), 3.88 (s, 2H), 3.71 (d, J=20.8 Hz, 4H), 3.32 (s, 2H), 2.94 (d, J=8.9 Hz, 2H), 2.61 (s, 2H), 2.53-2.46 (m, 1H), 2.37 (s, 1H), 2.28 (s, 1H), 2.06 (s, 1H), 2.01-1.83 (m, 10H), 1.54 (s, 1H), 1.39 (s, 9H), 1.20-1.06 (m, 1H), 0.96-0.60 (m, 9H). $^{13}$C NMR (151 MHz, DMSO) δ 172.1, 172.1, 171.4, 170.5, 170.4, 170.2, 170.1, 169.9, 169.9, 169.6, 168.7, 168.6, 168.3, 156.3, 155.3, 152.3, 144.7, 144.6, 144.0, 143.7, 143.6, 140.7, 140.6, 139.4, 137.7, 137.5, 132.2, 128.9, 128.6, 128.4, 128.3, 127.8, 127.6, 127.5, 127.4, 127.3, 127.1, 126.3, 125.5, 125.3, 123.8, 121.8, 121.4, 120.1, 116.8, 111.6, 109.7, 95.3, 80.7, 72.5, 71.5, 70.0, 69.5, 69.4, 66.2, 62.9, 59.7, 58.8, 58.2, 54.9, 54.7, 51.8, 48.1, 46.7, 42.9, 42.4, 39.5, 37.7, 35.2, 33.9, 27.6, 24.5, 20.7, 20.5, 15.5, 11.0, 10.2, 10.0. HRMS (ESI+) calcd, for $C_{90}H_{100}N_{10}NaO_{19}S^+$ $(M+Na)^+$: 1679.6779; found: 1679.6795.

Referring to the synthesis method of the compound 11a, 34.40 g of a white solid compound 11b was obtained, with a yield of 74%, $^1$H NMR (600 MHz, DMSO) δ 11.18 (d, J=8.8 Hz, 1H), 8.63 (s, 1H), 8.42 (s, 1H), 8.25 (d, J=40.3 Hz, 1H), 8.10 (d, J=34.1 Hz, 1H), 7.96 (d, J=14.3 Hz, 1H), 7.89 (s, 2H), 7.73 (d, J=6.4 Hz, 2H), 7.47 (d, J=9.2 Hz, 1H), 7.41 (d, J=3.0 Hz, 2H), 7.37-7.28 (m, 3H), 7.26-7.24 (m, 7H), 7.18-7.15 (m, 9H), 7.12-7.09 (m, 1H), 7.03-6.94 (m, 1H), 5.18 (s, 1H), 4.98-4.83 (m, 1H), 4.75 (s, 1H), 4.67 (d, J=5.9 Hz, 1H), 4.41-4.29 (m, 3H), 4.26-4.16 (m, 3H), 4.16-4.04 (m, 1H), 4.05-4.01 (m, 3H), 3.89-3.86 (d, J=15.7 Hz, 2H), 3.70 (d, J=18.8 Hz, 4H), 3.18-3.16 (m, 1H), 3.04-2.90 (m, 2H), 2.62-2.50 (m, 2H), 2.31 (d, J=54.1 Hz, 2H), 2.07 (s, 1H), 1.99-1.97 (m, 5H), 1.94-1.92 (m, 4H), 1.89-1.84 (m, 1H), 1.53 (s, 1H), 1.37 (s, 9H), 1.15-1.12 (m, 1H), 0.90-0.81 (m, 9H). $^{13}$C NMR (151 MHz, DMSO) & 172.0, 171.4, 170.4, 170.3, 170.2, 170.1, 169.9, 169.8, 169.7, 169.7, 168.6, 168.3, 162.3, 144.7, 143.9, 140.7, 136.8, 128.6, 127.6, 127.4, 127.1, 126.3, 125.3, 121.9, 120.0, 118.6, 116.2, 110.9, 80.7, 72.5, 71.9, 71.5, 69.5, 66.2, 65.9, 62.9, 62.9, 59.7, 58.8, 58.1, 54.8, 51.8, 48.1, 46.6, 42.8, 42.4, 37.9, 37.7, 35.76, 35.2, 33.9, 30.7, 27.6, 24.5, 20.7, 20.6, 15.4, 14.1, 11.0, 10.0. HRMS (ESI+) calcd, for $C_{83}H_{94}N_{10}NaO_{18}S^+$ $(M+Na)^+$: 1573.6360; found: 1573.6369.

Example 10: Synthesis of Compounds 12a and 12b

A principle was as follows:

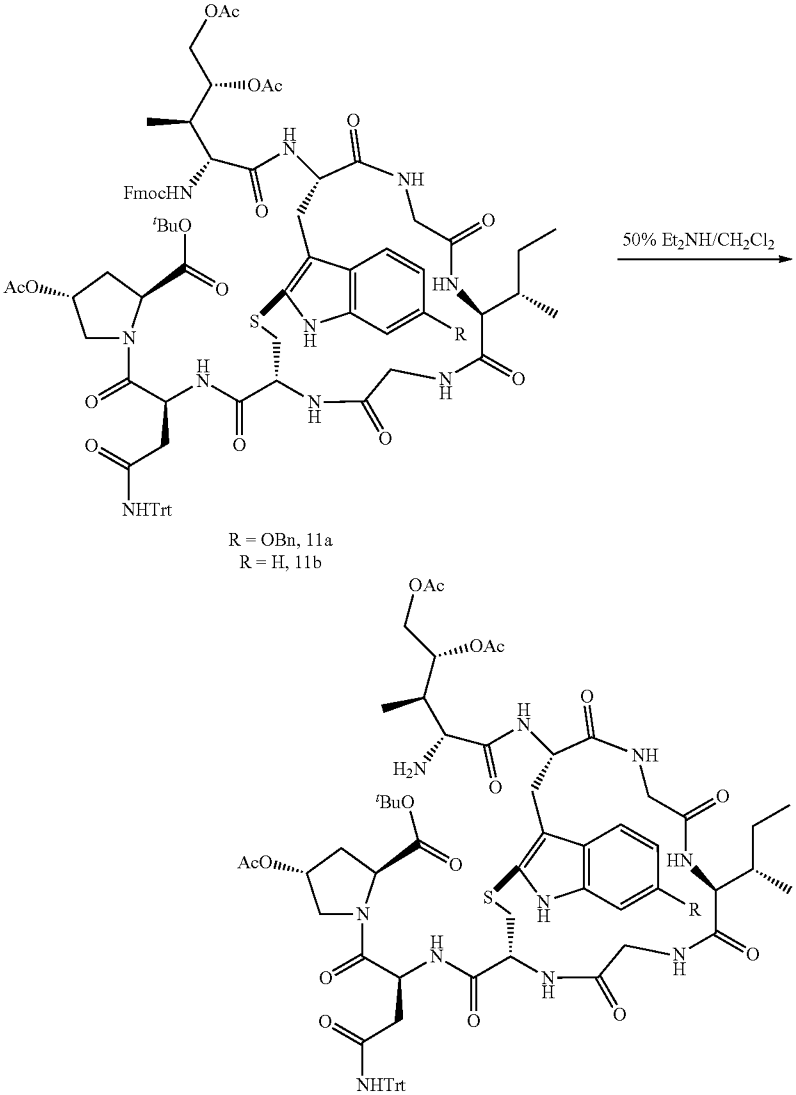

R = OBn, 11a
R = H, 11b

R = OBn, 12a
R = H, 12b

A 2,500 mL round-bottom flask was taken, and a magnetic stirring bar was placed in the 2,500 mL round-bottom flask. The compound 11a (49.70 g, 0.03 mol) was added to the 2,500 mL round-bottom flask, and an excess of 50 wt % of solution of DEA in DCM was added thereto. A resulting mixed solution was subjected to a reaction at room temperature for 2 h. After the reaction was completed, the solvent was removed under reduced pressure to obtain a crude product. The crude product was purified by 200-300 mesh silica gel column chromatography (a volume ratio of methanol/DCM being 2% to 4%) to obtain 34.80 g of a white solid compound 12a, with a yield of 81%.

$^1$H NMR (600 MHz, DMSO) δ 11.10-10.94 (m, 1H), 11.00 (s, 1H), 8.60 (s, 1H), 8.41-8.35 (m, 1H), 8.05-8.02 (m, 1H), 7.94 (d, J=37.2 Hz, 1H), 7.88-7.80 (m, 1H), 7.78-7.68 (m, 1H), 7.57 (d, J=22.5 Hz, 1H), 7.51 (d, J=12.6 Hz, 1H), 7.47 (d, J=7.2 Hz, 1H), 7.40 (d, J=7.1 Hz, 2H), 7.33 (dd, J=13.5, 6.7 Hz, 2H), 7.26-724 (m, 6H), 7.18-7.13 (m, 9H), 6.84 (s, 1H), 6.78-6.71 (m, 1H), 5.17 (s, 1H), 5.14-5.01 (m, 2H), 4.71-4.59 (m, 2H), 4.44-4.25 (m, 1H), 4.21 (t, J=7.9 Hz, 1H), 4.06 (dd, J=15.8, 9.1 Hz, 2H), 3.96-3.82 (m, 3H), 3.69 (d, J=16.5 Hz, 4H), 3.28 (s, 2H), 3.18 (s, 1H), 2.98-2.81 (m, 2H), 2.58 (s, 2H), 2.28 (s, 1H), 2.10-2.03 (m, 1H), 2.02-1.86 (m, 10H), 1.83-1.74 (m, 2H), 1.53 (s, 1H), 1.39 (s, 9H), 1.14 (d, J=6.8 Hz, 2H), 0.76 (m, 9H). $^{13}$C NMR (151 MHz, DMSO) δ 172.4, 171.3, 170.9, 170.4, 170.3, 170.0, 169.9, 169.8, 169.6, 169.5, 168.6, 168.3, 155.2, 144.7, 137.5, 128.6, 128.4, 128.3, 127.8, 127.6, 127.4, 127.3, 126.3, 123.7, 117.0, 111.5, 109.7, 95.3, 80.7, 72.4, 70.0, 69.5, 66.3, 58.6, 58.1, 54.8, 51.7, 48.1, 42.3, 39.5, 35.2, 33.9, 27.6, 24.3, 22.4, 20.7, 15.5, 11.1, 10.4, 9.5. HRMS (ESI+) calcd. for $C_{75}H_{91}N_{10}O_{17}S^+$ $(M+H)^+$: 1435.6279; found: 1435.6289.

Referring to the synthesis method of compound 12a, 22.32 g of a white solid compound 12b was obtained, with a yield of 84%, $^1$H NMR (600 MHz, DMSO) δ 11.23 (d, J=31.1 Hz, 1H), 8.73 (s, 1H), 8.61 (d, J=30.2 Hz, 1H), 8.41

(s, 1H), 8.33-8.24 (m, 1H), 8.05-7.97 (m, 2H), 7.89-7.79 (m, 1H), 7.76-7.72 (m, 1H), 7.68 (d, J=7.3 Hz, 1H), 7.57 (s, 1H), 7.30-7.24 (m, 6H), 7.20-7.12 (m, 9H), 7.04-6.98 (m, 1H), 5.19 (s, 1H), 4.89-4.79 (m, 1H), 4.73 (s, 1H), 4.69-4.51 (m, 2H), 4.28 (d, J=11.4 Hz, 1H), 4.21 (d, J=3.5 Hz, 1H), 4.15 (d, J=7.1 Hz, 1H), 4.09-3.99 (m, 1H), 3.97-3.81 (m, 3H), 3.78-3.59 (m, 4H), 3.53-3.40 (m, 1H), 3.27 (d, J=11.6 Hz, 1H), 3.23-3.11 (m, 1H), 3.00-2.84 (m, 1H), 2.74 (s, 1H), 2.59 (s, 1H), 2.36-2.24 (m, 1H), 2.15-1.99 (m, 4H), 1.98-1.90 (m, 8H), 1.84 (d, J=14.4 Hz, 1H), 1.57 (d, J=7.2 Hz, 2H), 1.39 (s, 9H), 1.20-1.08 (m, 1H), 0.96-0.64 (m, 9H). $^{13}C$ NMR (151 MHz, DMSO) δ 173.6, 171.8, 171.6, 171.4,
170.8, 170.6, 170.6, 170.5, 170.31, 170.2, 170.1, 170.0, 169.1, 168.9, 168.8, 168.7, 145.2, 145.2, 137.6, 129.1, 127.9, 126.8, 125.7, 122.6, 119.5, 118.9, 117.4, 111.4, 81.2, 73.0, 72.5, 69.9, 68.6, 66.9, 63.5, 60.2, 58.6, 55.4, 54.4, 52.3, 48.6, 44.2, 42.6, 38.1, 35.9, 35.6, 34.4, 28.1, 24.4, 22.9, 21.2, 16.1, 11.7, 10.0, 8.7. HRMS (ESI+) calcd, for $C_{68}H_{85}N_{10}O_{16}S^+$ $(M+H)^+$: 1329.5860; found: 1329.5867.
Example 11 Synthesis of Compounds 13a and 13b
A principle was as follows:
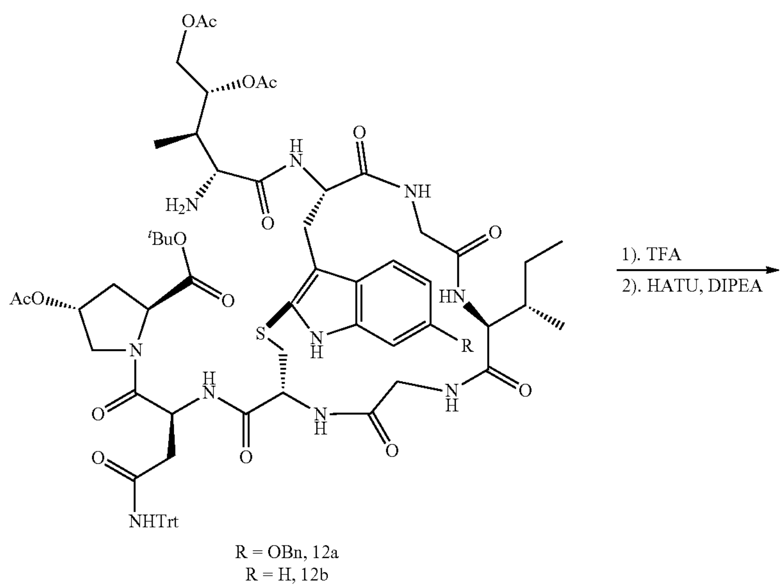
R = OBn, 12a
R = H, 12b
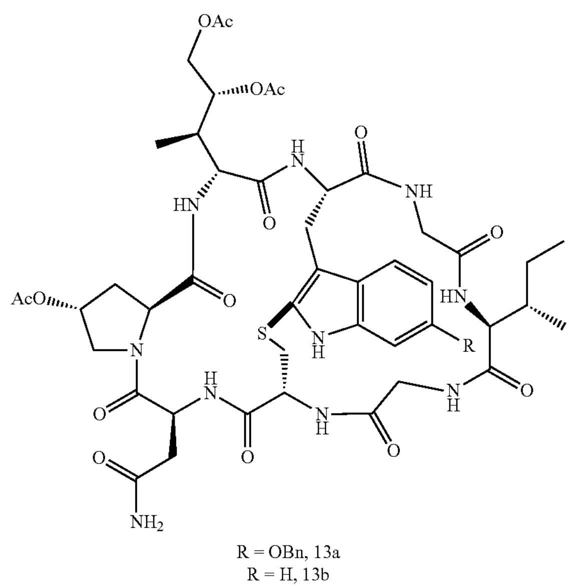
R = OBn, 13a
R = H, 13b A 2,500 mL round-bottom flask was taken, and a magnetic stirring bar was placed in the 2,500 mL round-bottom flask. The compound 12a (28.70 g, 0.02 mol) was added to the 2,500 mL round-bottom flask, and 200 mL of TFA was added thereto. A resulting mixture was stirred at room temperature for 0.5 h. The TFA was removed under reduced pressure to obtain a crude product. The crude product was directly used in the next synthesis step without further purification. The crude product was dissolved in dry DMF and stirred at zero degree for 5 min, followed by adding diisopropylethylamine (6.90 g, 2 equiv) and HATU (15.20 g, 2 equiv) thereto. A resulting mixture was heated to room temperature and subjected to a reaction for 12 h. After the reaction was completed, the solvent DMF was removed under reduced pressure to obtain a crude product. The crude product was purified by 200-300 mesh silica gel column chromatography (a volume ratio of methanol/DCM being 4% to 6%) to obtain 13.56 g of a white solid compound 13a, with a yield of 61%, $^1$H NMR (600 MHz, DMSO) δ 11.08 (d, J=42.1 Hz, 1H), 8.95 (s, 1H), 8.57 (s, 1H), 8.33 (d, J=12.6 Hz, 1H), 8.05 (d, J=11.8 Hz, 2H), 8.00-7.93 (m, 1H), 7.92-7.83 (m, 2H), 7.52 (d, J=7.1 Hz, 1H), 7.46 (t, J=7.2 Hz, 1H), 7.40 (t, J=7.4 Hz, 2H), 7.33-7.31 (m, 2H), 7.16 (dd, J=17.6, 8.8 Hz, 2H), 6.82-6.76 (m, 1H), 5.35 (s, 1H), 5.15-5.07 (m, 3H), 4.92-4.81 (m, 2H), 4.75 (s, 1H), 4.57 (d, J=9.8 Hz, 1H), 4.36-4.26 (m, 2H), 4.24-4.17 (m, 1H), 4.13-4.01 (m, 43H), 3.89 (dd, J=17.0, 6.7 Hz, 1H), 3.72 (s, 1H), 3.52-3.42 (m, 2H), 3.21-3.16 (m, 2H), 3.05-2.91 (m, 3H), 2.65-2.59 (m, 1H), 2.26 (s, 1H), 2.11 (t, J=11.0 Hz, 1H), 2.02 (s, 3H), 1.99 (s, 3H), 1.95 (s, 3H), 1.56 (s, 2H), 1.13-1.06 (m, 2H), 0.95 (dd, J=20.7, 9.5 Hz, 3H), 0.83 (t, J=6.9 Hz, 3H), 0.78 (d, J=6.0 Hz, 3H). $^{13}$C NMR (151 MHz, DMSO) δ 171.9, 171.9, 171.8, 171.1, 171.1, 170.6, 170.2, 169.9, 169.8, 169.8, 169.7, 169.6, 168.1, 167.5, 162.2, 158.7, 155.3, 151.9, 137.2, 128.4, 127.8, 127.4, 124.9, 123.6, 122.5, 121.7, 116.4, 109.9, 72.3, 71.0, 70.2, 69.5, 62.9, 61.8, 59.1, 54.9, 54.3, 53.0, 52.8, 52.5, 50.5, 39.5, 35.7, 34.4, 30.8, 28.9, 25.2, 20.9, 20.7, 20.6, 14.8, 11.2, 10.6. HRMS (ESI+) calcd, for $C_{52}H_{66}N_{10}O_{16}NaS^+$ (M+Na)$^+$: 1141.4271; found: 1141.4280.

Referring to the synthesis method of the compound 13a, 6.25 g of a white solid compound 13b was obtained, with a yield of 62%, $^1$H NMR (600 MHz, DMSO) δ 11.25 (s, 1H), 8.97 (s, 1H), 8.56 (s, 1H), 8.35 (s, 1H), 8.06 (d, J=14.9 Hz, 2H), 7.98 (d, J=9.9 Hz, 1H), 7.91 (d, J=7.0 Hz, 2H), 7.58 (d, J=7.7 Hz, 1H), 7.32 (s, 1H), 7.26 (d, J=7.9 Hz, 1H), 7.12 (t, J=7.3 Hz, 1H), 7.05-6.96 (m, 1H), 5.36 (s, 1H), 5.18 (d, J=13.7 Hz, 1H), 4.91 (s, 1H), 4.86 (d, J=7.7 Hz, 1H), 4.77 (d, J=8.0 Hz, 1H), 4.59 (t, J=9.2 Hz, 1H), 4.37-4.28 (m, 2H), 4.19 (dd, J=18.4, 7.9 Hz, 1H), 4.06 (dd, J=14.9, 9.6 Hz, 3H), 3.90 (dd, J=17.1, 6.9 Hz, 1H), 3.73 (s, 1H), 3.46 (d, J=17.8 Hz, 2H), 3.29-3.19 (m, 1H), 3.17 (s, 1H), 3.09-2.98 (m, 2H), 2.90 (dd, J=14.0, 7.3 Hz, 2H), 2.77 (d, J=8.1 Hz, 1H), 2.73 (s, 1H), 2.62 (s, 1H), 2.27 (d, J=6.4 Hz, 1H), 2.20-2.07 (m, 1H), 2.03 (s, 3H), 2.00 (s, 3H), 1.95 (s, 3H), 1.56 (d, J=6.9 Hz, 2H), 1.10 (d, J=6.4 Hz, 2H), 0.95 (d, J=6.5 Hz, 3H), 0.83 (d, J=6.8 Hz, 3H), 0.79 (d, J=6.0 Hz, 3H). $^{13}$C NMR (151 MHz, DMSO) δ 172.0, 171.9, 171.1, 170.7, 170.2, 169.9, 169.8, 169.7, 169.6, 168.2, 167.5, 136.5, 127.0, 124.3, 122.3, 120.1, 118.7, 116.1, 111.2, 72.3, 71.2, 62.9, 61.9, 59.1, 54.9, 53.0, 52.9, 52.5, 50.5, 42.3, 41.4, 38.3, 34.9, 34.4, 34.3, 33.6, 30.6, 29.0, 25.2, 21.0, 20.7, 20.6, 14.8, 11.2, 11.0, 10.6. HRMS (ESI+) calcd, for $C_{45}H_{60}N_{10}NaO_{15}S^+$ (M+Na)$^+$: 1035.3853; found: 1035.3869.

Example 12 Synthesis of Compound 14

A principle was as follows:

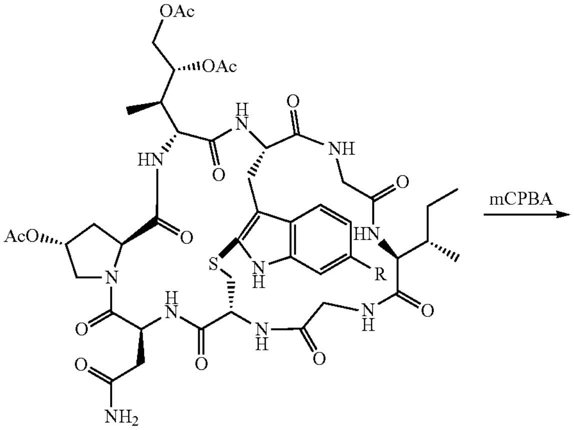

R = OBn, 13a
R = H, 13b

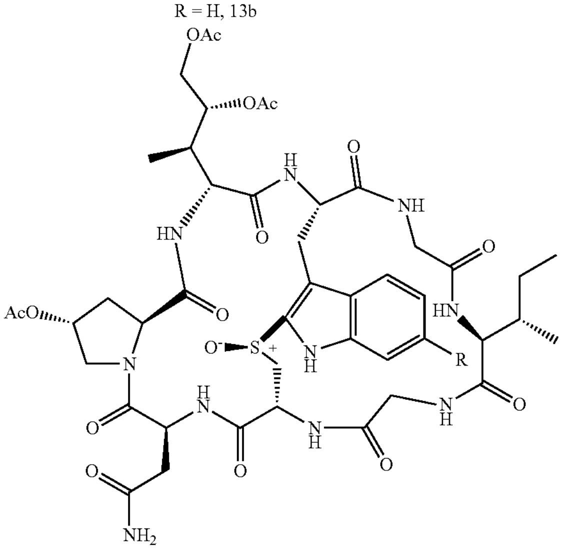

R = OBn, 14a
R = H, 14b

A 2,500 mL round-bottom flask was taken, and a magnetic stirring bar was placed in the 2,500 mL round-bottom flask. The compound 13a (5.60 g, 0.005 mol) was added to the 2,500 mL round-bottom flask, and 300 mL of a mixed solution of isopropanol and ethanol (a volume ratio of isopropanol to ethanol being 2:1) was added thereto. A resulting mixture was stirred in an ice-water bath for 10 min. A mixed solution of m-chloroperbenzoic acid in isopropanol and ethanol was added dropwise into a resulting reaction solution. A resulting mixture was subjected a reaction at zero degree for 30 min. After the reaction was completed, the mixed solution of isopropanol and ethanol was removed under reduced pressure to obtain a crude product. The crude product was purified by 200-300 mesh silica gel column chromatography (a volume ratio of methanol/DCM being 5% to 6%) to obtain 3.90 g of a white solid compound 14a, with a yield of 70%.

Referring to the synthesis method of the compound 14a, 3.00 g of a white solid compound 14b was obtained, with a yield of 73%, $^1$H NMR (600 MHz, DMSO) δ 11.67 (s, 1H), 8.88 (d, J=5.8 Hz, 1H), 8.55 (s, 1H), 8.30 (s, 1H), 8.26 (d, J=10.5 Hz, 2H), 7.89 (d, J=8.8 Hz, 1H), 7.85 (d, J=10.4 Hz, 1H), 7.81 (d, J=9.0 Hz, 1H), 7.65 (d, J=8.1 Hz, 1H), 7.44-7.38 (m, 2H), 7.19 (t, J=7.6 Hz, 1H), 7.09 (t, J=7.4 Hz, 1H), 5.33 (s, 1H), 5.21 (dd, J=19.6, 8.7 Hz, 1H), 5.04-4.99 (m, 1H), 4.91 (s, 1H), 4.85 (dd, J=10.4, 3.3 Hz, 1H), 4.76 (d, J=8.4 Hz, 1H), 4.32-4.24 (m, 3H), 4.07-4.00 (m, 3H), 3.89 (dd, J=17.3, 7.1 Hz, 1H), 3.70 (d, J=4.0 Hz, 1H), 3.48 (d, J=17.0 Hz, 2H), 3.41 (d, J=18.1 Hz, 1H), 3.25 (dd, J=15.1, 6.8 Hz, 2H), 3.10 (t, J=13.3 Hz, 1H), 2.93 (dd, J=10.1, 6.6 Hz, 2H), 2.79-2.69 (m, 1H), 2.57-2.51 (m, 1H), 2.24 (dd, J=13.6, 6.7 Hz, 1H), 2.12 (d, J=12.8 Hz, 1H), 2.02 (s, 3H), 1.98 (s, 3H), 1.95 (s, 3H), 1.58-1.50 (m, 2H), 1.12-1.03 (m, 2H), 0.92 (d, J=7.0 Hz, 3H), 0.82 (t, J=7.2 Hz, 3H), 0.79 (d, J=6.5 Hz, 3H). $^{13}C$ NMR (151 MHz, DMSO) δ 172.0, 171.7, 171.2, 170.5, 170.3, 170.2, 170.1, 169.8, 169.7, 169.6, 167.9, 166.9, 137.4, 132.3, 127.2, 123.2, 121.3, 119.5, 112.3, 110.8, 72.3, 71.1, 62.9, 61.9, 59.1, 52.9, 52.6, 52.4, 50.7, 49.9, 42.3, 41.1, 39.5, 36.8, 34.7, 34.6, 34.5, 32.9, 29.2, 25.2, 20.9, 20.7, 20.5, 14.8, 11.1, 10.8. HRMS (ESI+) calcd, for $C_{45}H_{60}N_{10}O_{16}NaS^+$ $(M+Na)^+$: 1051.3802; found: 1051.3816.
Example 13 Synthesis of Compound 1a
A principle was as follows:
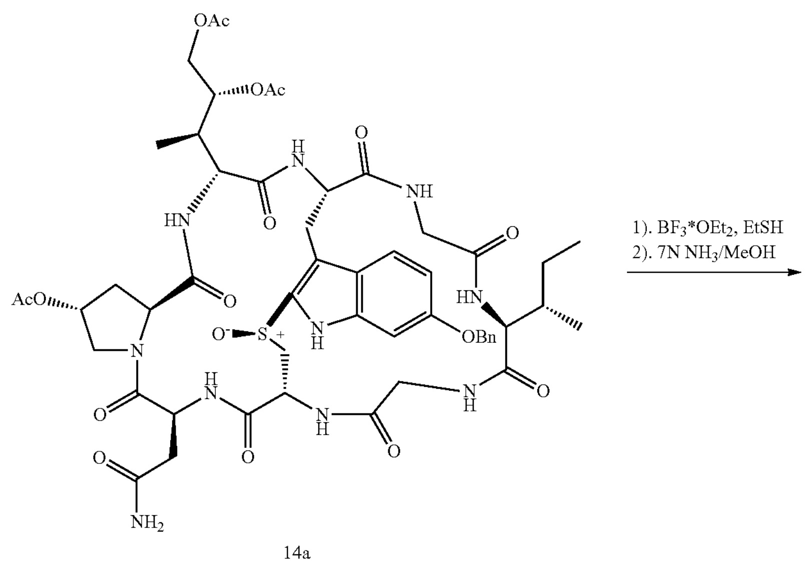
14a
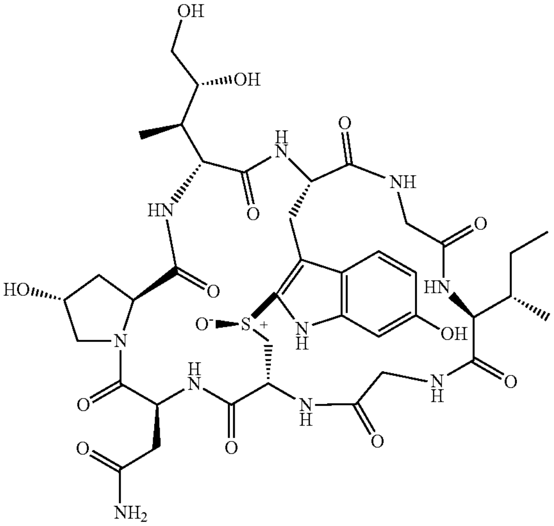
1a A 2,500 mL round-bottom flask was taken, and a magnetic stirring bar was placed in the 2,500 mL round-bottom flask. The compound 14a (4.00 g, 0.0045 mol) was added to the 2,500 mL round-bottom flask, an ethanethiol solution was added thereto, and followed by adding boron trifluoride diethyl etherate. After a reaction was conducted for 2 h, the solvent was removed by reduced pressure to obtain a benzyl deactivated crude product. Then the crude product was added with a 7 N methanol solution of ammonia. A resulting mixture was stirred at room temperature for 2 h. A reaction was monitored by TLC until the raw materials were consumed, and the methanol solution of ammonia was removed under reduced pressure to obtain 1.883 g of a product α-Amanitin 1a, with a yield of 50%.

4.84 (dd, J=9.8, 4.2 Hz, 1H), 4.65 (s, 1H), 4.41-4.36 (m, 3H), 4.25 (ddd, J=27.6, 14.9, 8.0 Hz, 2H), 3.90 (dd, J=17.3, 7.3 Hz, 1H), 3.81 (d, J=9.3 Hz, 1H), 3.73 (d, J=11.1 Hz, 1H), 3.68 (d, J=4.4 Hz, 1H), 3.45-3.44 (m, 3H), 3.41 (s, 1H), 3.32-3.27 (m, 1H), 3.23-3.18 (m, 1H), 3.17-3.15 (m, 1H), 3.07 (t, J=13.2 Hz, 1H), 2.98-2.91 (m, 2H), 2.74 (t, J=13.8 Hz, 1H), 2.22-2.15 (m, 2H), 1.86 (t, J=11.0 Hz, 1H), 1.59-1.50 (m, 2H), 1.15-1.06 (m, 1H), 0.85-0.77 (m, 9H). $^{13}$C NMR (151 MHz, DMSO) δ 171.9, 171.7, 171.1, 171.0, 170.8, 170.2, 169.9, 167.8, 167.0, 154.6, 138.8, 129.7, 122.0, 120.7, 111.5, 110.7, 96.7, 71.9, 68.6, 63.5, 62.1, 59.2, 55.8, 54.9, 53.9, 52.7, 50.8, 50.0, 48.6, 42.4, 41.3, 37.8, 37.3, 34.6, 33.4, 29.2, 25.2, 14.7, 11.4, 10.7.

Synthesis of Compound 1b:

A principle was as follows:

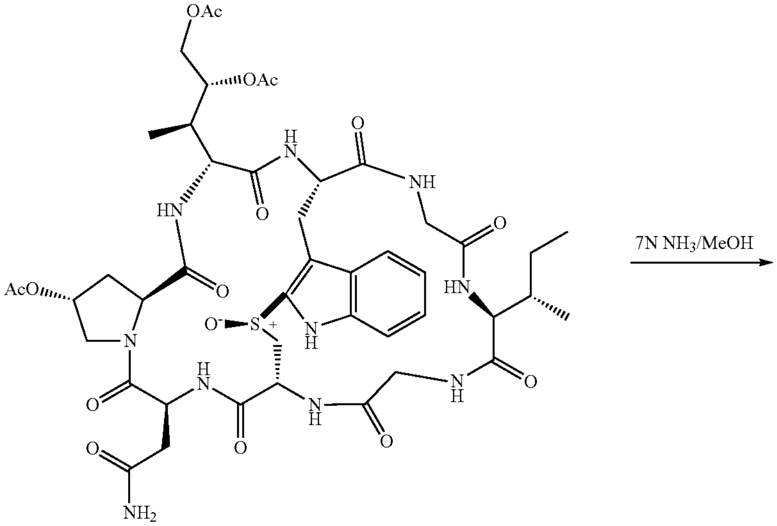

14b

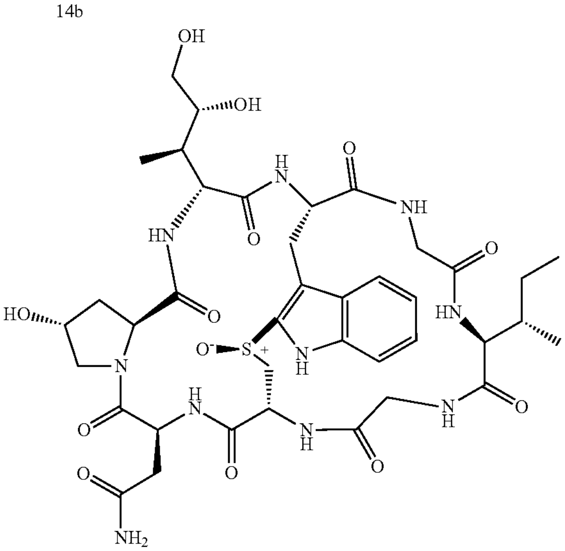

1b $^{1}$H NMR (600 MHz, DMSO) δ 11.25 (s, 1H), 9.21 (s, 1H), 8.77 (t, J=5.5 Hz, 1H), 8.56 (s, 1H), 8.37 (s, 1H), 8.24 (d, J=10.4 Hz, 1H), 8.21 (s, 1H), 7.92 (d, J=8.9 Hz, 1H), 7.84 (d, J=8.6 Hz, 1H), 7.67 (d, J=9.8 Hz, 1H), 7.42 (d, J=8.7 Hz, 1H), 7.37 (s, 1H), 6.75 (s, 1H), 6.61 (d, J=8.6 Hz, 1H), 5.18 (s, 1H), 5.09 (dd, J=19.7, 8.4 Hz, 1H), 4.98-4.92 (m, 1H),

A 2,500 mL round-bottom flask was taken, and a magnetic stirring bar was placed in the 2,500 mL round-bottom flask. The compound 14b (3.00 g, 0.003 mol) was added to the 2,500 mL round-bottom flask, and a 7 N methanol solution of ammonia was added thereto. A resulting mixed solution was stirred at room temperature for 2 h. A reaction was monitored by TLC until the raw materials were consumed, and the methanol solution of ammonia was removed under reduced pressure to obtain a crude product. The crude product was purified by 200-300 mesh silica gel column chromatography (a volume ratio of methanol/DCM being 10% to 15%) to obtain 1.92 g of a white solid compound Amaninamide 1b, with a yield of 74%, $^1$H NMR (600 MHz, DMSO) δ 11.80-11.03 (m, 1H), 8.82 (s, 1H), 8.57 (s, 1H), 8.40 (s, 1H), 8.29 (d, J=10.3 Hz, 1H), 8.22 (d, J=23.3 Hz, 1H), 7.94 (t, J=12.5 Hz, 1H), 7.86 (dd, J=26.5, 7.9 Hz, 1H), 7.69-7.62 (m, 2H), 7.40 (d, J=7.7 Hz, 2H), 7.18 (dd, J=19.6, 11.9 Hz, 1H), 7.08 (t, J=7.5 Hz, 1H), 5.33-5.22 (m, 1H), 5.16 (dd, J=19.6, 8.3 Hz, 1H), 5.04-4.96 (m, 1H), 4.85 (dd, J=9.7, 4.2 Hz, 1H), 4.66 (s, 1H), 4.44-4.369 (m, 3H), 4.30-4.18 (m, 2H), 3.90 (dd, J=17.3, 7.3 Hz, 1H), 3.79 (dd, J=29.6, 10.1 Hz, 2H), 3.68 (d, J=4.3 Hz, 1H), 3.50-3.35 (m, 8H), 3.31 (dd, J=10.9, 5.7 Hz, 8H), 3.28-3.19 (m, 11H), 3.13 (d, J=13.2 Hz, 1H), 2.95 (t, J=10.5 Hz, 2H), 2.79 (dd, J=27.3, 10.7 Hz, 2H), 2.23-2.16 (m, 2H), 1.86 (t, J=10.9 Hz, 1H), 1.55 (d, J=6.1 Hz, 2H), 1.13-1.04 (m, 2H), 0.80 (dd, J=22.1, 5.0 Hz, 9H). $^{13}$C NMR (151 MHz, DMSO) δ 171.9, 171.7, 171.21, 171.0, 170.8, 170.2, 169.9, 167.9, 167.0, 137.4, 132.4, 127.2, 123.1, 121.5, 119.4, 112.3, 110.9, 71.9, 68.7, 63.5, 62.10, 59.2, 58.9, 55.8, 54.0, 52.6, 50.9, 49.9, 42.4, 41.7, 41.0, 39.5, 37.3, 34.6, 33.4, 29.2, 25.2, 14.8, 11.4, 10.7. HRMS (ESI+) calcd, for $C_{39}H_{54}N_{10}NaO_{13}S^+$ (M+Na)$^+$: 925.3482; found: 925.3489.

The above described are merely preferred embodiments of the present disclosure rather than limitations to the present disclosure in any form. It should be noted that those of ordinary skill in the art may further make several improvements and modifications without departing from the principle of the present disclosure, but such improvements and modifications should be deemed as falling within the protection of the present disclosure.

What is claimed is:

1. A method for preparing a cyclic peptide toxin compound α-Amanitin and/or Amaninamide, α-Amanitin having a structure as shown in Formula 1a, and Amaninamide having a structure as shown in Formula 1b:

Formula 1a

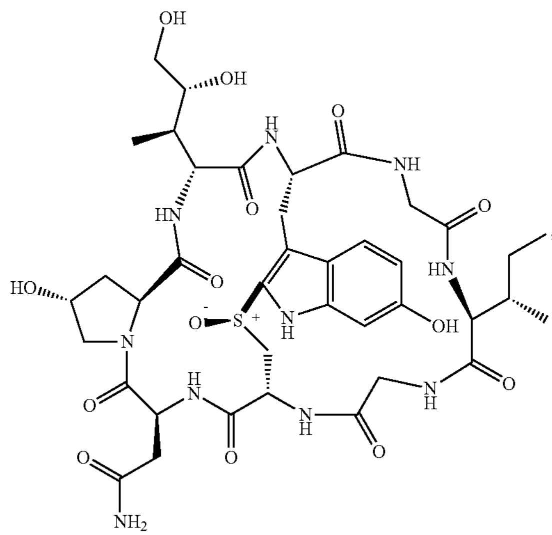

-continued

Formula 1b

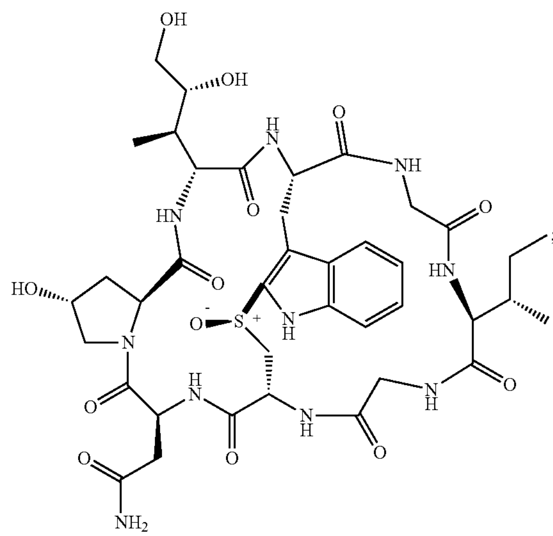

wherein the method comprises the following steps:

step 1, subjecting a compound 2 to acetylation and esterification to obtain a compound 3;

step 2, subjecting the compound 3 to condensation and deprotection to obtain a compound 4;

step 3, subjecting the compound 4 to condensation and deprotection to obtain a compound 5;

step 4, subjecting the compound 5 to condensation and deprotection to obtain a compound 6;

step 5, subjecting the compound 6 to condensation and deprotection to obtain a compound 7;

step 6, subjecting the compound 7 to condensation and deprotection to obtain a compound 8;

step 7, subjecting the compound 8 to condensation and deprotection to obtain a compound 9;

step 8, subjecting the compound 9 to condensation and deprotection to obtain a compound 10;

step 9, subjecting the compound 10 to carbon-sulfur bond ring closure in an iodine-mediated manner to obtain a compound 11;

step 10, subjecting the compound 11 to deprotection to obtain a compound 12;

step 11, subjecting the compound 12 to deprotection and condensation to obtain a compound 13;

step 12, subjecting the compound 13 to oxidation to obtain a compound 14; and step 13, subjecting the compound 14 to deprotection to obtain the cyclic peptide toxin compounds α-Amanitin and Amaninamide;

the compounds 2 to 14 have the following structures, respectively:

2

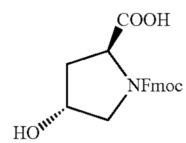

-continued
3
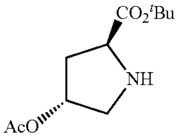
4
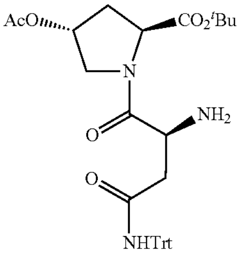
5
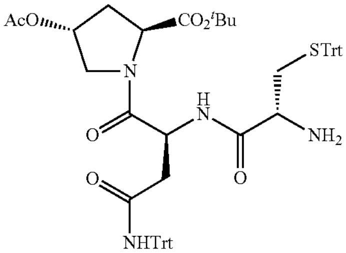
6
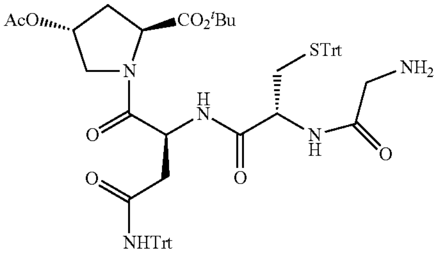
7
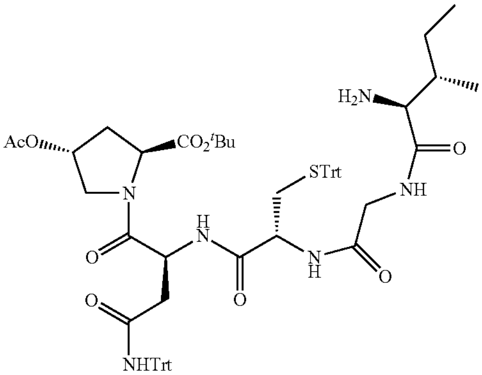
-continued
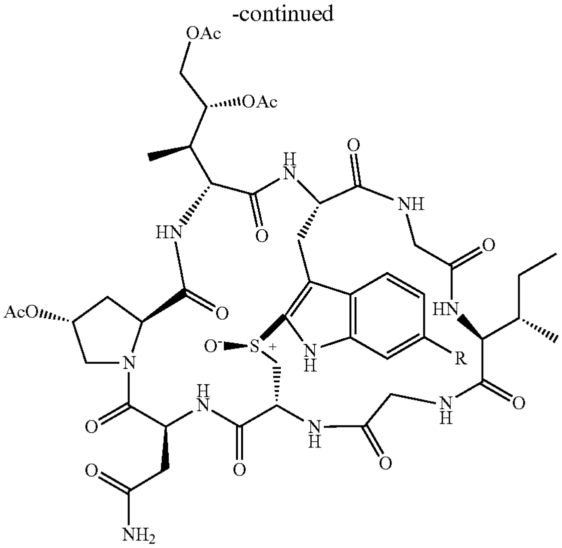
14
8
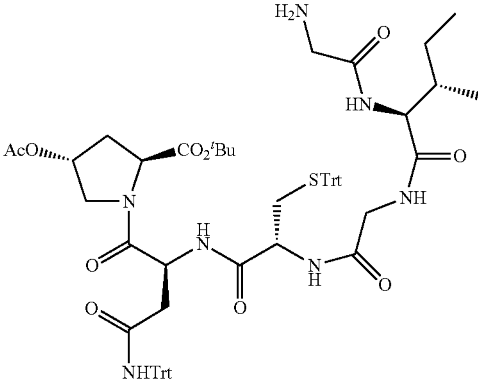
9
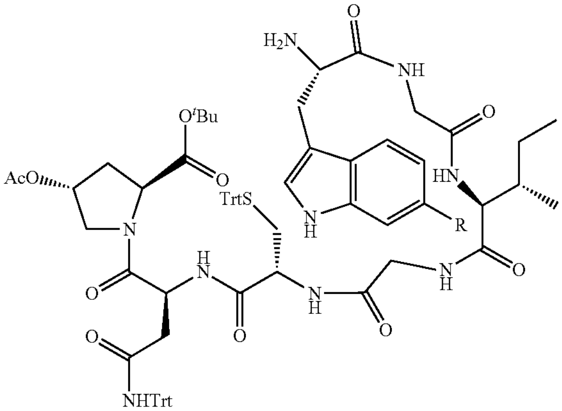

-continued

10

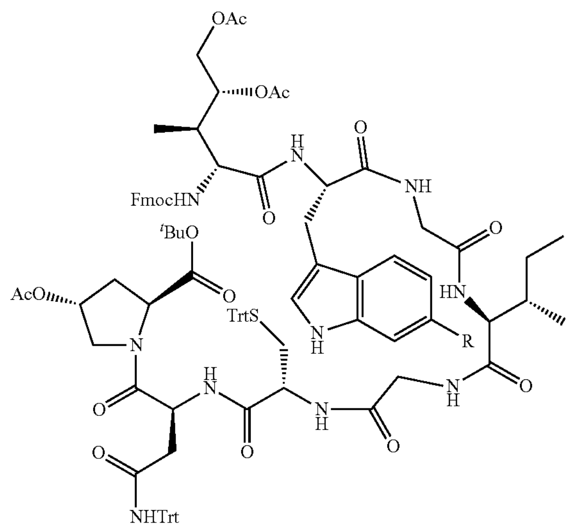

11

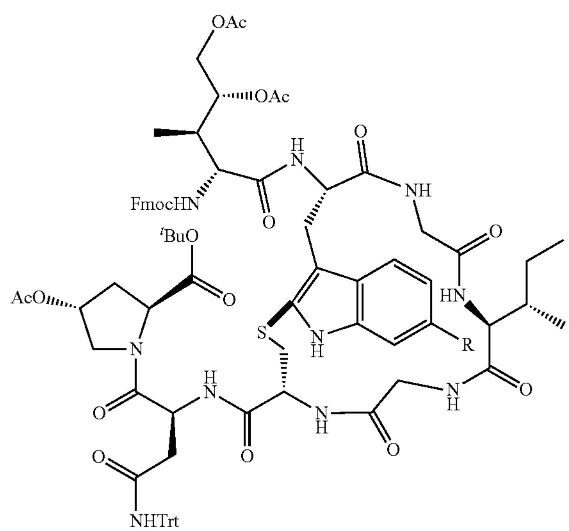

12

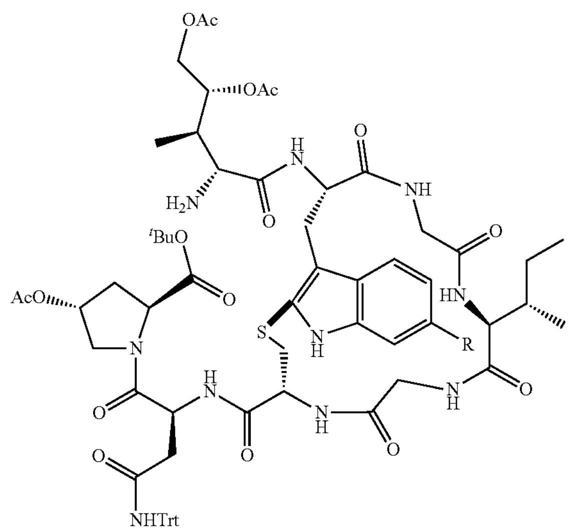

-continued

13

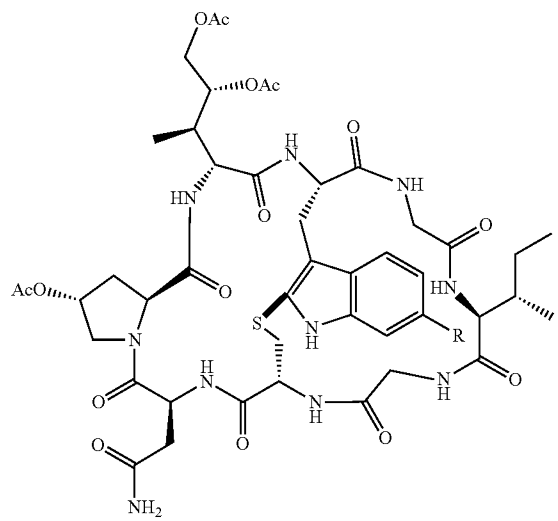

14

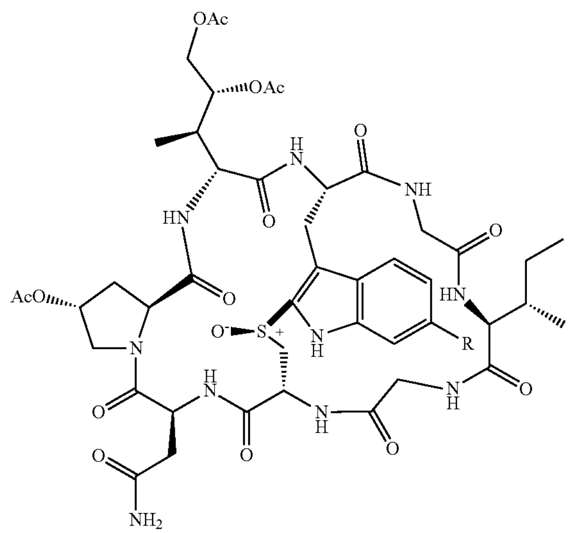

wherein R in the compounds 9 to 14 is selected from the group consisting of —H and —OBn.

2. The method of claim 1, comprising the following steps:

step 1, mixing the compound 2, pyridine, acetyl chloride, and an organic solvent, conducting the acetylation to obtain an acetylated product, mixing the acetylated product with N,N-dimethylpyridine and di-tert-butyl dicarbonate (BOC), and conducting the esterification to obtain the compound 3;

step 2, mixing the compound 3, N-fluorenylmethyl (Fmoc)-asparagine, 1-hydroxybenzotriazole, 1-ethyl-(3-dimethylaminopropyl)carbodiimide hydrochloride (EDC-HCl), and an organic solvent, and conducting the condensation and the deprotection to obtain the compound 4;

step 3, mixing the compound 4, N-Fmoc-cysteine, 1-hydroxybenzotriazole, EDC-HCl, and an organic solvent, and conducting the condensation and the deprotection to obtain the compound 5;

step 4, mixing the compound 5, N-Fmoc-glycine, 1-hydroxybenzotriazole, EDC-HCl, and an organic solvent, and conducting the condensation and the deprotection to obtain the compound 6;

step 5, mixing the compound 6, N-Fmoc-isoleucine, 1-hydroxybenzotriazole, EDC-HCl, and an organic solvent, and conducting the condensation and the deprotection to obtain the compound 7;

step 6, mixing the compound 7, N-Fmoc-glycine, 1-hydroxybenzotriazole, EDC-HCl, and an organic solvent, and conducting the condensation and the deprotection to obtain the compound 8;

step 7, mixing the compound 8, a compound 15, 1-hydroxybenzotriazole, EDC-HCl, and an organic solvent, and conducting the condensation and the deprotection to obtain the compound 9, the compound 15 being selected from the group consisting of N-Fmoc-6-benzyloxytryptophan and N-Fmoc-tryptophan;

step 8, mixing the compound 9, a (2S,3R,4R)-4,5-dihydroxyisoleucine derivative, 1-hydroxybenzotriazole, EDC-HCl, and an organic solvent, and conducting the condensation and the deprotection to obtain the compound 10;

step 9, under a protective atmosphere, mixing the compound 10 and an organic solution of iodine, and conducting the carbon-sulfur bond ring closure to obtain the compound 11;

step 10, mixing the compound 11 and an organic solvent, and conducting the deprotection to obtain the compound 12;

step 11, mixing the compound 12, diisopropylethylamine, 2-(7-azabenzotriazol-1-yl)-N,N,N',N'-tetramethyluronium hexafluorophosphate (HATU), and an organic solvent, and conducting the deprotection and the condensation to obtain the compound 13;

step 12, mixing the compound 13, m-chloroperbenzoic acid, and an organic solvent, and conducting the oxidation to obtain the compound 14; and step 13, under the condition that R is —OBn, subjecting the compound 14, ethanethiol, and a boron trifluoride diethyl etherate solution to a reaction to obtain a crude product, and mixing the crude product and a solution of ammonia in an alcohol, and conducting the deprotection to obtain the α-Amanitin; alternatively, under the condition that R is —H, mixing the compound 14 and the solution of ammonia in the alcohol, and conducting the deprotection to obtain the Amaninamide.

3. The method of claim 2, wherein in step 1, a molar ratio of the compound 2, the acetyl chloride, and the pyridine is in a range of 1:1-3:1-5, and a molar ratio of the compound 2, the N,N-dimethylpyridine, and the BOC is in a range of 1:0.1-1:1-5;

in step 2, a molar ratio of the compound 3, the N-Fmoc-asparagine, the 1-hydroxybenzotriazole, and the EDC-HCl is 1:1.1:1.1:1.1;

in step 3, a molar ratio of the compound 4, the N-Fmoc-cysteine, the 1-hydroxybenzotriazole, and the EDC-HCl is 1:1.1:1.1:1.1;

in step 4, a molar ratio of the compound 5, the N-Fmoc-glycine, the 1-hydroxybenzotriazole, and the EDC-HCl is 1:1.1:1.1:1.1;

in step 5, a molar ratio of the compound 6, the N-Fmoc-isoleucine, the 1-hydroxybenzotriazole, and the EDC-HCl is 1:1.1:1.1:1.1;

in step 6, a molar ratio of the compound 7, the N-Fmoc-glycine, the 1-hydroxybenzotriazole, and the EDC-HCl is 1:1.1:1.1:1.1;

in step 7, a molar ratio of the compound 8, the compound 15, the 1-hydroxybenzotriazole, and the EDC-HCl is 1:1.1:1.1:1.1;

in step 8, a molar ratio of the compound 9, the (2S,3R,4R)-4,5-dihydroxyisoleucine derivative, the 1-hydroxybenzotriazole, and the EDC-HCl is 1:1.1:1.1:1.1;

in step 9, a molar ratio of the compound 10 to iodine in the organic solution of iodine is 1:4, and the organic solution of iodine has a concentration of 2 mg/ml; and in step 10, the organic solvent is a solution of diethylamine (DEA) in dichloromethane (DCM), the DEA in the solution of DEA in DCM has a mass fraction of 50%, and the compound 11 has a concentration of 0.1 g/mL in the solution of DEA in DCM.

4. The method of claim 2, wherein in step 11, a molar ratio of the compound 12, the diisopropylethylamine, and the HATU is 1:2.2:2.

5. The method of claim 2, wherein in step 13, the solution of ammonia in the alcohol has a concentration of 7 mol/L.

6. The method of claim 1, wherein in step 1, the acetylation is conducted at 0° C. for 2 h.

7. The method of claim 1, wherein in step 1, the esterification is conducted at room temperature for 0.5 h.

8. The method of claim 1, wherein in step 2, the condensation and the deprotection are conducted at room temperature for 12 h;

in step 3, the condensation and the deprotection are conducted at room temperature for 12 h;

in step 4, the condensation and the deprotection are conducted at room temperature for 12 h;

in step 5, the condensation and the deprotection are conducted at room temperature for 12 h;

in step 6, the condensation and the deprotection are conducted at room temperature for 12 h;

in step 7, the condensation and the deprotection are conducted at room temperature for 12 h;

in step 8, the condensation and the deprotection are conducted at room temperature for 12 h;

in step 9, the carbon-sulfur bond ring closure is conducted at room temperature for 1 h;

in step 10, the deprotection is conducted at room temperature for 1 h;

in step 11, the condensation and the deprotection are conducted at room temperature for 12 h; and in step 12, the oxidation is conducted at room temperature for 0.5 h.

9. The method of claim 1, wherein in step 1, after the acetylation is completed, the method further comprises: quenching the acetylation with a saturated ammonium chloride solution, adjusting a resulting reaction solution to a pH value of 2 with dilute hydrochloric acid and then extracting three times with DCM to obtain organic phases, combining the organic phases and then drying over anhydrous sodium sulfate, and removing a solvent under reduced pressure to obtain a crude product.

10. The method of claim 1, wherein in step 1, after the esterification is completed, the method further comprises: decompressing a resulting product to remove tert-butanol (TBA) to obtain a crude product, dissolving the crude product in a DCM/DEA solution, stirring at room temperature for 1 h, removing a solvent under reduced pressure, and subjecting a resulting material to separation by column chromatography to obtain the compound 3.

11. The method of claim 1, wherein in step 2, after the condensation and the deprotection are completed, the method further comprises: washing a resulting organic phase with a saturated sodium carbonate solution, drying over anhydrous sodium sulfate, and removing a solvent under reduced pressure to obtain a crude product; and dissolving the crude product in a DCM/DEA solution, stirring at room temperature for 1 h, removing a solvent under reduced pressure, and subjecting a resulting material to separation by column chromatography to obtain the compound 4.

12. The method of claim 1, wherein in step 3, after the condensation and the deprotection are completed, the method further comprises: washing a resulting organic phase with a saturated sodium carbonate solution, drying over anhydrous sodium sulfate, and removing a solvent under reduced pressure to obtain a crude product; and dissolving the crude product in a DCM/DEA solution, stirring at room temperature for 1 h, removing a solvent under reduced pressure, and subjecting a resulting material to separation by column chromatography to obtain the compound 5.

13. The method of claim 1, wherein in step 4, after the condensation and the deprotection are completed, the method further comprises: washing a resulting organic phase with a saturated sodium carbonate solution, drying over anhydrous sodium sulfate, and removing a solvent under reduced pressure to obtain a crude product; and dissolving the crude product in a DCM/DEA solution, stirring at room temperature for 1 h, removing a solvent under reduced pressure, and subjecting a resulting material to separation by column chromatography to obtain the compound 6.

14. The method of claim 1, wherein in step 5, after the condensation and the deprotection are completed, the method further comprises: washing a resulting organic phase with a saturated sodium carbonate solution, drying over anhydrous sodium sulfate, and removing a solvent under reduced pressure to obtain a crude product; and dissolving the crude product in a DCM/DEA solution, stirring at room temperature for 1 h, removing a solvent under reduced pressure, and subjecting a resulting material to separation by column chromatography to obtain the compound 7.

15. The method of claim 1, wherein in step 6, after the condensation and the deprotection are completed, the method further comprises: washing a resulting organic phase with a saturated sodium carbonate solution, drying over anhydrous sodium sulfate, and removing a solvent under reduced pressure to obtain a crude product; and dissolving the crude product in a DCM/DEA solution, stirring at room temperature for 1 h, removing a solvent under reduced pressure, and subjecting a resulting material to separation by column chromatography to obtain the compound 8.

16. The method of claim 1, wherein in step 7, after the condensation and the deprotection are completed, the method further comprises: washing a resulting organic phase with a saturated sodium carbonate solution, drying over anhydrous sodium sulfate, and removing a solvent under reduced pressure to obtain a crude product; and dissolving the crude product in a DCM/DEA solution, stirring at room temperature for 1 h, removing a solvent under reduced pressure, and subjecting a resulting material to separation by column chromatography to obtain the compound 9.

17. The method of claim 1, wherein in step 8, after the condensation and the deprotection are completed, the method further comprises: washing a resulting organic phase with a saturated sodium carbonate solution, drying over anhydrous sodium sulfate, removing a solvent under reduced pressure to obtain a crude product, and subjecting the crude product to separation by column chromatography to obtain the compound 10.

18. The method of claim 1, wherein in step 9, after the carbon-sulfur bond ring closure is completed, the method further comprises: removing N,N-dimethylformamide (DMF) under reduced pressure and recovering to obtain a crude product, and subjecting the crude product to separation by column chromatography to obtain the compound 11.

19. The method of claim 1, wherein in step 10, after the deprotection is completed, the method further comprises: removing a solvent under reduced pressure to obtain a crude product, and subjecting the crude product to separation by column chromatography to obtain the compound 12.

20. Intermediates 4 to 14 prepared by the method of claim 1, wherein the intermediates 4 to 14 have the following structures, respectively:

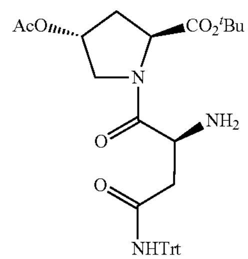

4

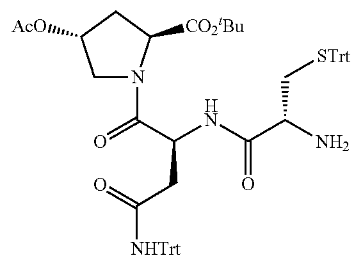

5

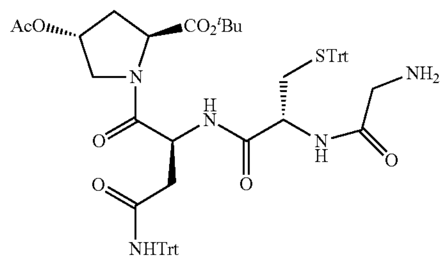

6

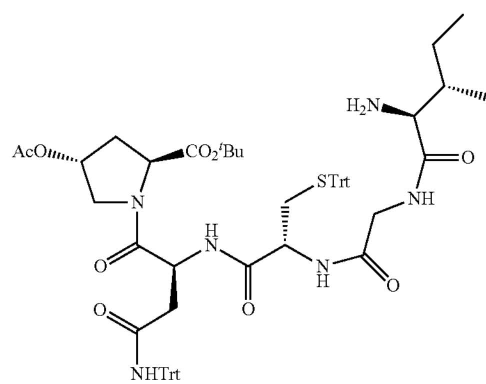

7

-continued
8
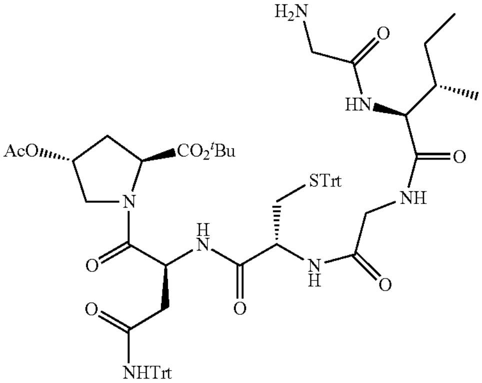
9
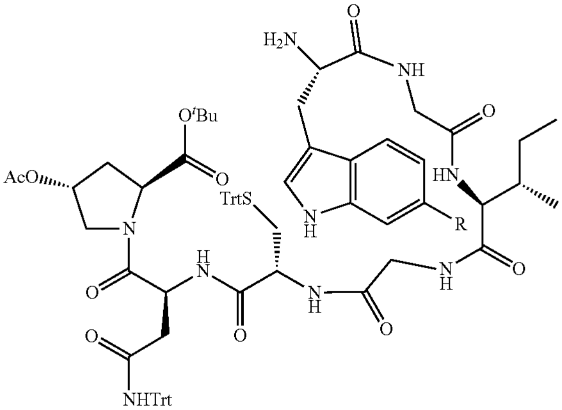
10
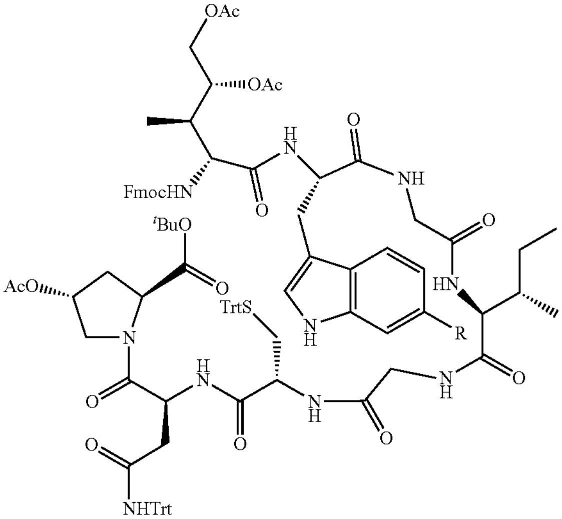
-continued
11
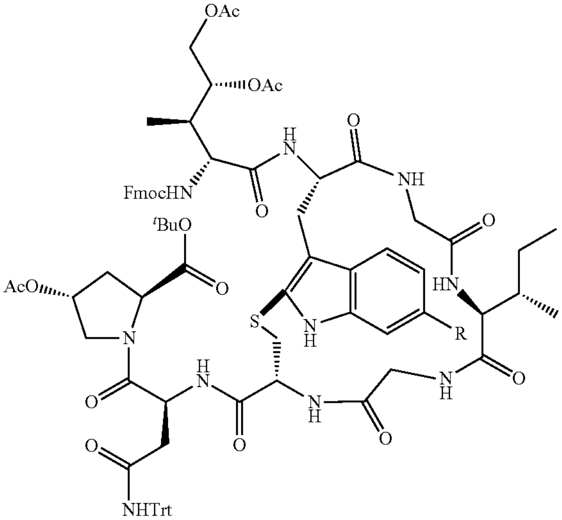
12
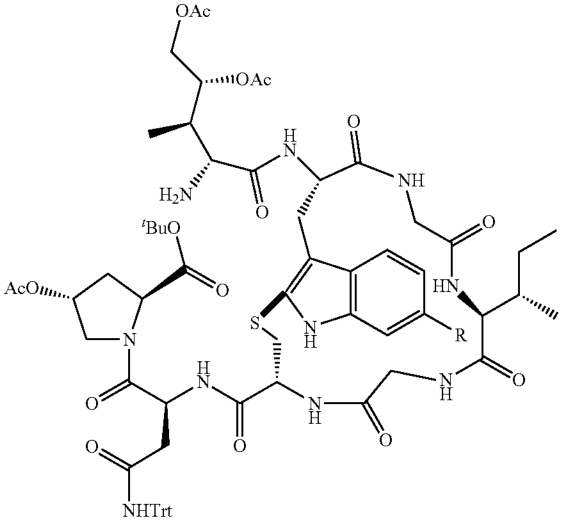
13
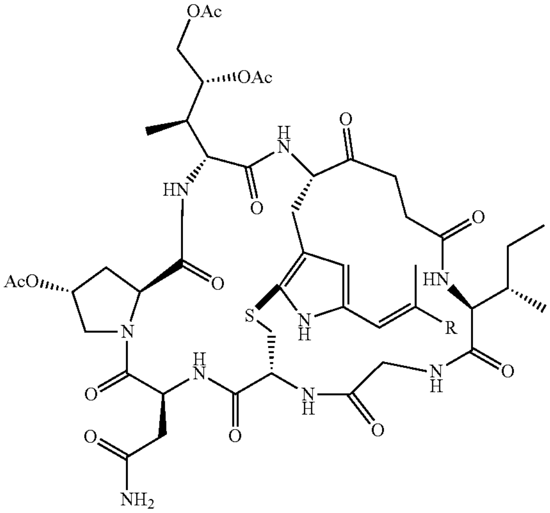

-continued
14
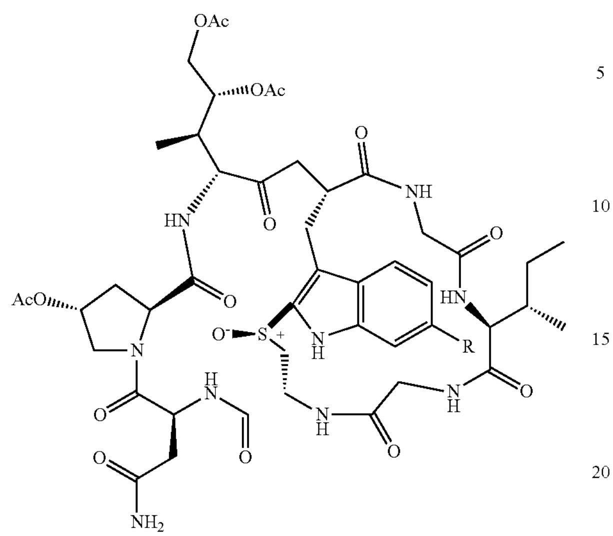
wherein R in the compounds 9 to 14 is selected from the group consisting of —H and —OBn.
* * * * *